(12) United States Patent
Huang et al.

(10) Patent No.: US 9,952,173 B2
(45) Date of Patent: Apr. 24, 2018

(54) LEAD ION SENSORS, METHODS OF MAKING AND USES THEREOF

(71) Applicant: TONGJI UNIVERSITY, Shanghai (CN)

(72) Inventors: Meirong Huang, Shanghai (CN); Yongbo Ding, Shanghai (CN); Xingui Li, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 0 days.

(21) Appl. No.: 15/021,917

(22) PCT Filed: Sep. 30, 2013

(86) PCT No.: PCT/CN2013/084750
§ 371 (c)(1),
(2) Date: Mar. 14, 2016

(87) PCT Pub. No.: WO2015/042971
PCT Pub. Date: Apr. 2, 2015

(65) Prior Publication Data
US 2016/0231271 A1    Aug. 11, 2016

(51) Int. Cl.
*G01N 27/333* (2006.01)
*C08G 73/02* (2006.01)
(Continued)

(52) U.S. Cl.
CPC ....... *G01N 27/3335* (2013.01); *C08G 73/026* (2013.01); *C08G 73/0266* (2013.01);
(Continued)

(58) Field of Classification Search
CPC .................. G01N 27/333; C08G 73/0266
See application file for complete search history.

(56) References Cited

U.S. PATENT DOCUMENTS 5,093,439 A * 3/1992 Epstein .............. C08G 73/0266
252/500
5,354,816 A * 10/1994 Shimizu .............. C08G 73/0266
525/535
(Continued)

FOREIGN PATENT DOCUMENTS

| CN | 101643544 | 2/2010 |
| CN | 101717507 | 6/2010 |

(Continued)

OTHER PUBLICATIONS

Li et al. (Anal. Chem. 2012, 84, 134-140).*
(Continued)

*Primary Examiner* — Liam J Heincer
(74) *Attorney, Agent, or Firm* — Dorsey & Whitney LLP

(57) ABSTRACT

Copolymers including at least one optionally substituted 2-hydroxy-5-sulfonic aniline as a first constituent unit and at least one optionally substituted phenylenediamine as a second constituent unit are disclosed. Compositions containing the copolymers, and methods of making the copolymers are also disclosed. The compositions can also contain for example an ethylene-vinyl acetate copolymer (EVA) and/or electrical conducting additives. The compositions can, for example, be used for detecting lead ions in a sample.

38 Claims, 17 Drawing Sheets

(51) Int. Cl.

| | | |
|---|---|---|
| *C08G 73/06* | (2006.01) | |
| *C08J 5/22* | (2006.01) | |
| *G01N 27/403* | (2006.01) | |
| *C08L 23/08* | (2006.01) | |
| *C08L 27/06* | (2006.01) | |
| *C08L 27/02* | (2006.01) | |
| *C08L 31/04* | (2006.01) | |
| *C08L 79/02* | (2006.01) | |
| *C08L 79/04* | (2006.01) | |

(52) U.S. Cl.
CPC ..... *C08G 73/0273* (2013.01); *C08G 73/0694* (2013.01); *C08J 5/2231* (2013.01); *C08J 5/2256* (2013.01); *C08J 5/2275* (2013.01); *C08L 23/0853* (2013.01); *C08L 27/02* (2013.01); *C08L 27/06* (2013.01); *C08L 31/04* (2013.01); *G01N 27/4035* (2013.01); *C08J 2323/08* (2013.01); *C08J 2327/06* (2013.01); *C08J 2329/04* (2013.01); *C08J 2331/04* (2013.01); *C08J 2365/02* (2013.01); *C08J 2433/20* (2013.01); *C08J 2479/02* (2013.01); *C08L 79/02* (2013.01); *C08L 79/04* (2013.01)

(56) References Cited

U.S. PATENT DOCUMENTS

| | | | | |
|---|---|---|---|---|
| 5,589,108 | A * | 12/1996 | Shimizu | C08G 73/0266 252/500 |
| 5,980,784 | A * | 11/1999 | Shimizu | C08G 61/122 252/500 |
| 8,361,323 | B2 * | 1/2013 | Huang | C02F 1/285 210/674 |
| 2008/0131909 | A1 * | 6/2008 | Clark | B82Y 5/00 435/7.1 |
| 2009/0142274 | A1 * | 6/2009 | Clark | B82Y 5/00 424/9.6 |
| 2011/0269920 | A1 * | 11/2011 | Min | B01J 20/28007 525/540 |
| 2012/0009419 | A1 * | 1/2012 | Tran | B82Y 30/00 428/401 |
| 2012/0211702 | A1 * | 8/2012 | Epstein | H01B 1/128 252/500 |
| 2012/0277397 | A1 * | 11/2012 | Huang | C02F 1/285 528/172 |
| 2013/0209667 | A1 * | 8/2013 | Yamada | C08L 79/02 427/58 |
| 2014/0183061 | A1 * | 7/2014 | Huang | C08J 5/22 205/789 |
| 2014/0183062 | A1 * | 7/2014 | Huang | C08L 79/04 205/789.5 |
| 2015/0273404 | A1 * | 10/2015 | Hoek | C08K 5/17 525/540 |
| 2016/0223909 | A1 * | 8/2016 | Nagasawa | G03F 7/2059 |
| 2016/0304744 | A1 * | 10/2016 | Park | B29C 41/12 |

FOREIGN PATENT DOCUMENTS

| | | |
|---|---|---|
| WO | WO/2012/145885 | 11/2012 |
| WO | WO/2013/075327 | 5/2013 |

OTHER PUBLICATIONS

Huang et al. (Talanta 85, 2011, 1575-1584).*
International Search Report and Written Opinion from International Application No. PCT/CN2013/084750 dated Jul. 8, 2014.
Abbaspour A et al "A highly selective and sensitive disposable carbon composite PVC based membrane for determination of lead ion in environmental samples" Journal of Hazardous Materials vol. 174 Issues 1-3 pp. 656 to 661 Available online Sep. 23, 2009.
Anastasova I S et al. "Development of miniature all solid state potentiometric sensing system" Sensors and Actuators B Chemical vol. 146 Issue 1 pp. 1 to 33 Apr. 8, 2010.
Gupta V K et al "PVC based membranes of NN-dibenzyl 1 4 10 13 tetraoxa7 16diazacyclooctadecane as Pb II selective sensor" Sensors and Actuators B Chemical vol. 120 Issue 1 pp. 259 to 265 Available online Mar. 29, 2009.
Huang M R et al "Development of potentiometric lead ion sensors based on ionophores bearing oxygen sulfur containing functional groups" Chinese Journal of Analytical Chemistry vol. 40 Issue 1 pp. 50 to 58 Jan. 2012.
Huang M R et al "Facile synthesis of polysulfoaminoanthraquinone anosorbents for rapid removal and ultrasensitive fluorescent detection of heavy metal ions" Journal of Physical Chemistry vol. 115 Issue 13 pp. 5301 to 5315 Mar. 16, 2011.
Huang M R et al "Lead ion selective electrodes based on polyphenylenediamine as unique solid ionophores" Talanta, vol. 85 Issue 3 pp. 1575 to1584 Available online Jun. 25, 2011.
Ion I et al "Polyvinyl chloride-based membranes of 3 7 11tris 2pyridylmethyl 3 7 11 17tetraazabicyclo 11 3 1 heptadeca1 17 13 15triene as a Pb II selective sensor" Desalination vol. 259 Issues 1 to 3 pp. 38 to 43 Available online May 14, 2010.
Li X G et al "Ultrasensitive Pb II potentiometric sensor based on copoaniline nanoparticles in a plasticizer free membrane with a long lifetime" Analytical Chemistry vol. 84 Issue 1 pp. 134 to 140 Nov. 20, 2011.
Lisak G "New polyacrylate based lead II ion selective electrodes" Microchimica Acta vol. 164 Issue 3 pp. 293 to 297 Available online Aug. 28, 2008.
Michalska A "Poly n butyl acrylate based lead II selective electrodes" Talanta vol. 79 Issue 5 pp. 1247 to 1251 Available online May 23, 2009.
Wilson D et al "Lead II ion selective electrodes with PVC membranes based on two bisthioureas as ionophores 1 3bis Nbenzoylthioureido benzene and 1 3bis Nfuroylthioureidobenzene" Journal of Hazardous Materials vol. 181 Issues 1 to 3 pp. 140 to 146 Available online May 2, 2010.

* cited by examiner

LEAD ION SENSORS, METHODS OF MAKING AND USES THEREOF

CROSS-REFERENCE TO RELATED APPLICATION

This Application is a U.S. National Stage filing under 35 U.S.C. § 371 of International Application No. PCT/CN2013/08475, filed on Sep. 30, 2013, the entire disclosure of which is hereby incorporated by reference for all purposes in its entirety.

BACKGROUND

The present application relates to compositions and methods for detecting metal ions, such as lead ions, in a sample.

Over the past decades, many analytical techniques have been developed for quantitatively determining trace lead ions. Potentiometric ion selective electrodes (ISEs) are known to be a low-cost tool for sensitive and rapid determination of lead ions. However, the traditional polyvinyl chloride (PVC)-based potentiometric sensor has been restricted to micromolar range due to the undesired leaching and uptake effects.

Various ISEs, for example ISEs with plasticizer-free polymers including polyacrylate, silicone rubber and polyurethane, have been made to address the limitations of PVC-based ISEs. However, these ISEs have their own challenges. For example, acrylate polymers are not commercially available and must be synthesized via photopolymerization, and silicone rubber and polyurethane are generally incompatible with reported ionophores. There is a need for developing long-lasting electrode sensors that allows reliable detections and measurements for metal ions in a sample at trace levels.

SUMMARY

In some embodiments, there is provided a copolymer comprising at least one optionally substituted 2-hydroxy-5-sulfonic aniline as a first constituent unit and at least one optionally substituted phenylenediamine as a second constituent unit. In some embodiments, there is provided a composition comprising microparticles, wherein the microparticles comprise the copolymer.

Some embodiments provide a method of making a copolymer, the method comprising: forming a composition comprising at least one oxidizing agent, at least one optionally substituted 2-hydroxy-5-sulfonic aniline monomer, and at least one optionally substituted phenylenediamine monomer; and maintaining the composition under conditions effective to polymerize the 2-hydroxy-5-sulfonic aniline monomer and the optionally substituted phenylenediamine monomer to form the copolymer.

In some embodiments, there is provided a composition comprising a copolymer and a polymer matrix, wherein the copolymer comprises at least one optionally substituted 2-hydroxy-5-sulfonic aniline as a first constituent unit and at least one optionally substituted phenylenediamine as a second constituent unit.

Further disclosed in some embodiments is a polymeric membrane for ion sensitive measurement comprising an ethylene-vinyl acetate copolymer (EVA) and one or more ionophores that are selective toward lead ions.

Some embodiments provide a method of making a polymeric membrane for ion sensitive measurement, the method comprising: forming a composition comprising a polymer matrix and one or more ionophores that are selective toward lead ions, wherein the one or more ionophores comprise at least one optionally substituted 2-hydroxy-5-sulfonic aniline as a first constituent unit and at least one optionally substituted phenylenediamine as a second constituent unit; maintaining the composition under conditions effective to form a polymeric composition; and casting the polymeric composition to a solid surface to form a polymeric membrane.

In some embodiments, there is provided a sensor for measuring lead ions, the sensor comprising: a lead ion-selective electrode, wherein the lead ion-selective electrode comprises a polymer matrix and a copolymer, wherein the copolymer comprises at least one optionally substituted 2-hydroxy-5-sulfonic aniline as a first constituent unit and at least one optionally substituted phenylenediamine as a second constituent unit.

Some embodiments provide a method for detecting lead ions in a sample, the method comprising: providing a sample suspected of containing one or more lead ions; contacting the sample with a sensor, wherein the sensor comprises a reference electrode and a lead ion-selective electrode, wherein the lead ion-selective electrode comprises a polymer matrix and one or more ionophores selective for lead ions, wherein the one or more ionophores comprise a copolymer comprising at least one optionally substituted 2-hydroxy-5-sulfonic aniline as a first constituent unit and at least one optionally substituted phenylenediamine as a second constituent unit; and measuring an electromotive force (EMF) between the reference electrode and the lead ion-selective electrode.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION

Figure 1:
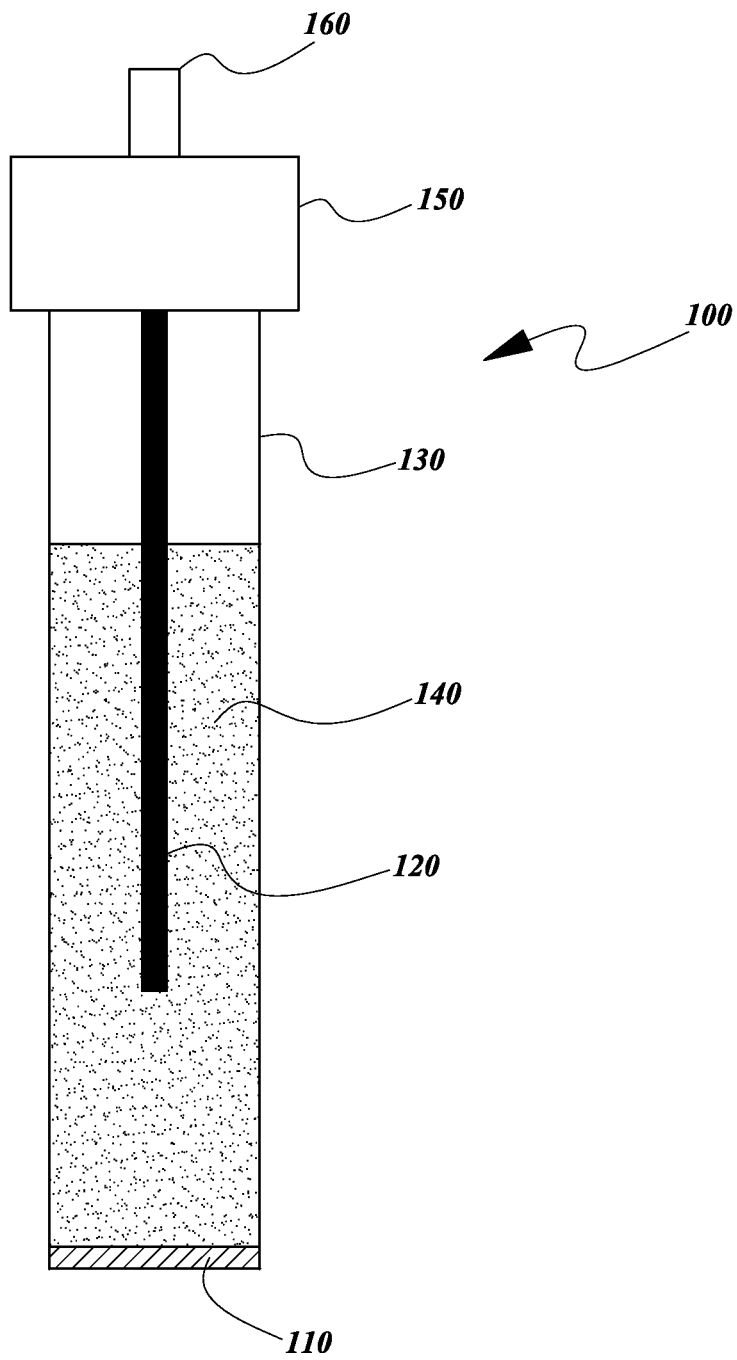
FIG. 1 depicts an illustrative embodiment of a lead ion selective electrode (Pb(II) ISE).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Disclosed herein are copolymers having at least one optionally substituted 2-hydroxy-5-sulfonic aniline as a first constituent unit and at least one optionally substituted phenylenediamine as a second constituent unit, and compositions including one or more of the copolymers. Methods for making the copolymer and the compositions are disclosed herein. Also disclosed herein are polymeric membranes for ion sensitive measurement, where the polymeric membranes contain an ethylene-vinyl acetate polymer (EVA) and one or more ionophore that are selective toward lead ions (sometimes written as Pb(II) or $Pb^{2+}$). The compositions and polymeric membranes can be used, for example, to detect metal ions, including lead ions, in a sample. Also disclosed are methods of using the copolymers, compositions and polymeric membranes.

Definitions

As used herein, the term "electron donating" refers to the ability of a substituent to donate electrons relative to that of hydrogen if the hydrogen atom occupied the same position in the molecule. This term is well understood by one skilled in the art and discussed in Advanced Organic Chemistry by M. Smith and J. March, John Wiley and Sons, New York N.Y. (2007). Non-limiting examples of electron donating groups include $C_{1-6}$ alkyl (such as —$CH_3$ and —$CH_2CH_3$), —OH, $C_{1-6}$ alkoxy (such as —$OCH_3$ and —$OCH_2CH_3$), hydroxyalkyl (such as —$CH_2OH$, —$CH_2CH_2OH$), alkylthio (such as —$SCH_3$), carbamate (such as (—$NHC(O)OCH_3$ and (—$NHC(O)OCH_2CH_3$), —$N(CH_3)_2$, —$N(CH_2CH_3)_2$, —$NH_2$, and —SH.

As used herein, "alkyl" refers to a straight or branched hydrocarbon chain that has a fully saturated (i.e., contains no double or triple bonds) hydrocarbon group. The alkyl group of the compounds may be designated as "$C_{1-4}$ alkyl" or similar designations. By way of example only, "$C_{1-4}$ alkyl" indicates that there are one to four carbon atoms in the alkyl chain, for example, the alkyl chain is selected from methyl, ethyl, propyl, iso-propyl, n-butyl, isobutyl, sec-butyl, and tert-butyl. Typical alkyl groups include, but are in no way limited to, methyl, ethyl, propyl, isopropyl, butyl, isobutyl, tertiary butyl, pentyl, hexyl, and the like. The alkyl group may be substituted or unsubstituted.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like. A non-limiting example of alkylthion is —$SCH_3$.

As used herein, an "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl. A non-limiting example includes free amino (i.e., —$NH_2$).

As used herein, "carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl. Examples of carbamate include, but are not limited to, methylcarbamate (—$NHC(O)OCH_3$), ethylcarbamate (—$NHC(O)OCH_2CH_3$), benzylcarbamate (—$NHC(O)OCH_2C_6H_5$), and the like.

As used herein, "hydroxyalkyl" refers to an alkyl group substituted with one or more hydroxy groups. Non-limiting examples of hydroxyalky include hydroxymethyl and 2,3-dihydroxybutyl.

As used herein, the "operating lifetime" of a sensing membrane in a Pb(II) selective sensor refers to the time interval between the conditioning of the sensing membrane and the moment when the slope of the potential response curve of the sensor drops below 95% of its original response slope. Accordingly, the sensing membrane is considered to be unusable when the slope of its potential response curve becomes lower than 95% of its original response slope.

As used herein, a composition that is "substantially plasticizer free" is a composition that contains less than about 1 weight percentage (for example, 1 wt %) plasticizer(s) based on the total weight of the composition. For example, the composition that is substantially plasticizer free can contain no plasticizer.

Poly(PD-Co-HSA) Copolymers

As used herein, "poly(PD-co-HSA) copolymers" refer to copolymers that include at least one optionally substituted 2-hydroxy-5-sulfonic aniline as a first constituent unit and at least one optionally substituted phenylenediamine as a second constituent unit.

In some embodiments, the first constituent unit is represented by Formula I:

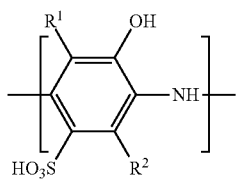

(I)

In some embodiments, $R^1$ is hydrogen or an electron-donating group, and $R^2$ is hydrogen or an electron-donating group. $R^1$ can be, for example, —NHC(O)OCH$_2$CH$_3$, —CH$_3$, —NH$_2$, or hydrogen. $R^2$ can be, for example, —CH$_3$, —NH$_2$, or hydrogen. In some embodiments, $R^1$ is hydrogen and $R^2$ is hydrogen. In some embodiments, $R^1$ is —CH$_3$ and $R^2$ is hydrogen. In some embodiments, $R^1$ is —NH$_2$ and $R^2$ is hydrogen. In some embodiments, $R^1$ is —NHC(O)OCH$_2$CH$_3$ and $R^2$ is hydrogen.

In some embodiments, the first constituent unit is 2-hydroxy-5-sulfonic aniline represented by Formula

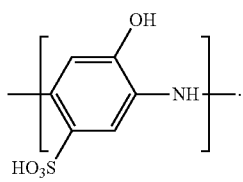

Non-limiting examples of the first constituent unit include:

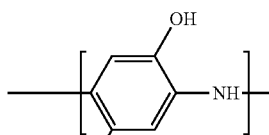

,

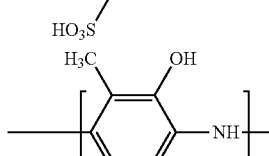

,

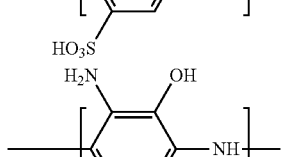

, and

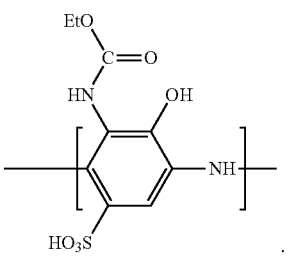

.

In some embodiments, the second constituent unit is represented by Formula II:

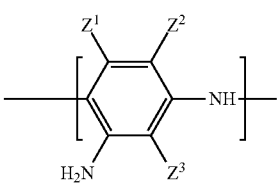

(II)

In some embodiments, $Z^1$ is hydrogen, —NH$_2$, —CH$_3$, —OH, —OCH$_3$, or —CH$_2$OH. In some embodiments, $Z^2$ is hydrogen, —OCH$_3$, or —SCH$_3$. In some embodiments, $Z^3$ is hydrogen, —OCH$_3$, or —CH$_3$.

Examples of the second constituent unit represented by Formula II include, but are not limited to

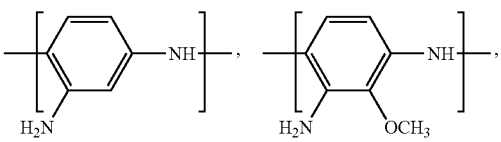

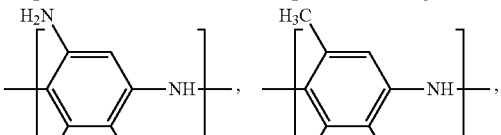

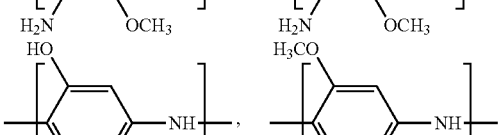

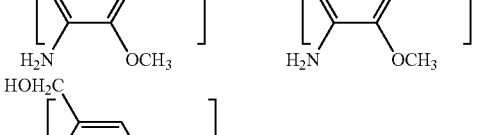

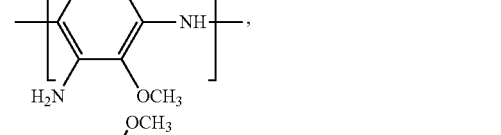

, and

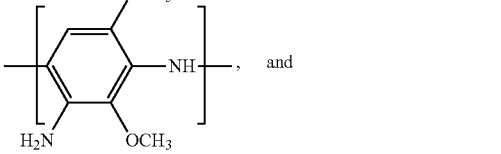

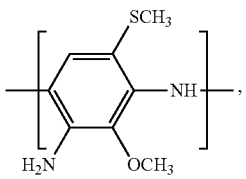

In some embodiments, the second constituent unit is represented by Formula III, Formula IV, or Formula V:

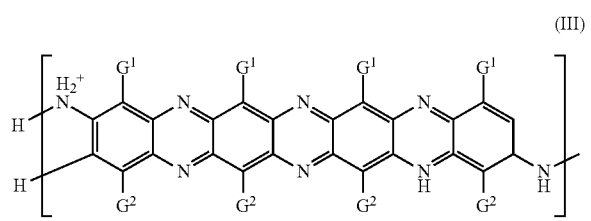
(III)

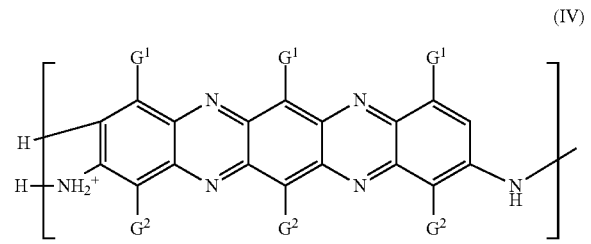
(IV)

-continued

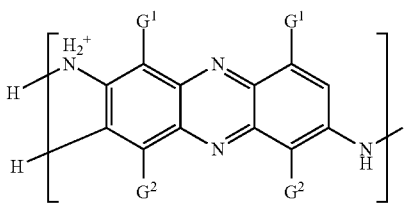
(V)

$G^1$ and $G^2$ can be each independently hydrogen or an electron-donating group. In some embodiments, $G^1$ and $G^2$ are each independently hydrogen or methoxy.

As disclosed herein, non-limiting examples of electron donating groups include $C_{1-6}$ alkyl (such as —$CH_3$ and —$CH_2CH_3$), —OH, $C_{1-6}$ alkoxy (such as —$OCH_3$ and —$OCH_2CH_3$), an amino group (such as —$NH_2$), $C_{1-6}$ hydroxyalkyl (such as hydroxymethyl), $C_{1-6}$ alkylthio (such as —$SCH_3$), —$N(CH_3)_2$, —$N(CH_2CH_3)_2$, a carbamate (such as —$NHC(O)OCH_2CH_3$), and —SH. In some embodiments, the electron-donating group is $C_{1-6}$ alkyl or $C_{1-6}$ alkoxy. In some embodiments, the electron-donating group is —$CH_3$, —$CH_2CH_3$, —OH, —$OCH_3$, —$OCH_2CH_3$, —$N(CH_3)_2$, —$N(CH_2CH_3)_2$, or —SH. In some embodiments, the electron-donating group is $CH_3$, —$NH_2$, or —$NHC(O)OCH_2CH_3$. In some embodiments, the electron-donating group is —$NH_2$, —$CH_3$, —OH, —$OCH_3$, or —$CH_2OH$. In some embodiments, the electron-donating group is —$OCH_3$, —$CH_3$, or —$SCH_3$.

In some embodiments, the poly(PD-co-HSA) copolymer is represented by Formula:

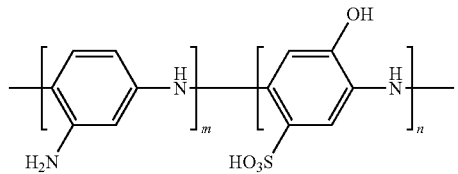

In some embodiments, the poly(PD-co-HSA) copolymer is represented by Formula:

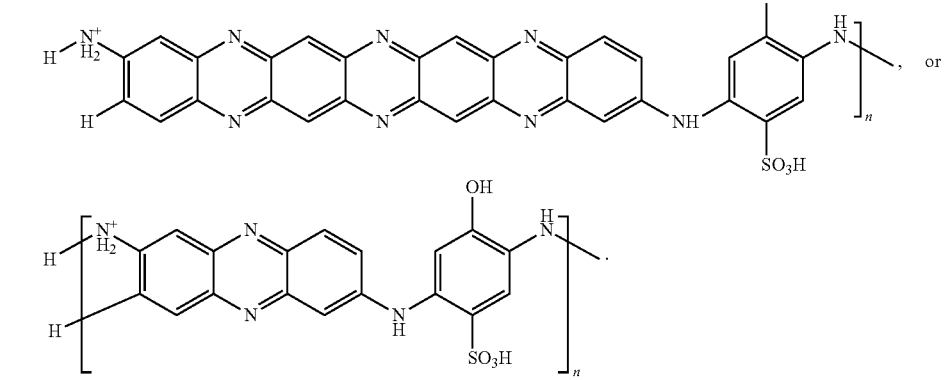

The content of the first constituent unit and the second constituent unit in the poly(PD-co-HSA) copolymers disclosed herein can vary. The first constituent unit can be present in the poly(PD-co-HSA) copolymer, for example, in an amount of about 0.5% to about 50% by mole. For example, the amount of the first constituent may be about 0.5%, about 1%, about 2%, about 3%, about 4%, about 5%, about 6%, about 7%, about 8%, about 9%, about 10%, about 12%, about 15%, about 20%, about 30%, about 40%, about 50% by mole, or a range between any two of these values. In some embodiments, the first constituent unit can be present in the poly(PD-co-HSA) copolymer in an amount of about 0.5% to about 10% by mole. In some embodiments, the first constituent unit is present in the copolymer in an amount of about 5% to about 10% by mole.

The second constituent unit, for example, can be present in the poly(PD-co-HSA) copolymer in an amount of about 50% to about 99.9% by mole. The second constituent unit, for example, can be present in the poly(PD-co-HSA) copolymer in an amount of about 50%, about 60%, about 70%, about 80%, about 90%, about 91%, about 92%, about 93%, about 94%, about 95%, about 96%, about 97%, about 98%, about 99%, about 99.5%, about 99.9% by mole, or a range between any two of these values. In some embodiments, the second constituent unit is present in the copolymer in an amount of about 90% to about 95% by mole.

The molar ratio of the first constituent unit and the second constituent unit in the poly(PD-co-HSA) copolymers disclosed herein can also vary. For example, the poly(PD-co-HSA) copolymer can have a molar ratio of the first constituent unit to the second constituent unit of about 1:99 to about 50:50. In some embodiments, the poly(PD-co-HSA) copolymer has a molar ratio of the first constituent unit to the second constituent unit of about 1:99, about 5:95, about 10:90, about 20:80, about 30:70, about 40:60, about 50:50, or a range between any two of these values. In some embodiments, the poly(PD-co-HSA) copolymer has a molar ratio of the first constituent unit to the second constituent unit of about 5:95 to about 10:90. In some embodiments, the poly(PD-co-HSA) copolymer has a molar ratio of the first constituent unit to the second constituent unit of about 5:95.

Some embodiments disclosed herein include particles that include one or more of poly(PD-co-HSA) copolymers, for example any one or more of the poly(PD-co-HSA) copolymers described herein. In some embodiments, the poly(PD-co-HSA) copolymer is present as particles, such as microparticles. Compositions comprising the poly(PD-co-HSA) particles are also disclosed herein.

The size of the poly(PD-co-HSA) copolymer particles can vary. For example, the poly(PD-co-HSA) copolymer particles can have an average diameter of about 10 nm to about 5 μm. In some embodiments, the poly(PD-co-HSA) copolymer particles can have an average diameter of about 10 nm, about 100 nm, about 200 nm, about 300 nm, about 400 nm, about 500 nm, about 600 nm, about 700 nm, about 800 nm, about 900 nm, about 1 μm, about 1.5 μm, about 2 μm, about 2.5 μm, about 3 μm, about 3.5 μm, about 4 μm, about 4.5 μm, about 5 μm, or a range between any two of these values. In some embodiments, the poly(PD-co-HSA) copolymer particles can have an average diameter of 10 nm to about 5 μm, about 50 nm to about 4 μm, about 500 nm to about 3 μm, or about 1 μm to 2 μm. In some embodiments, the poly(PD-co-HSA) copolymer particles have an average diameter of about 500 nm, about 700 nm, about 900 nm, about 1100 nm, about 1600 nm, about 2000 nm, or a range between any two of these values. In some embodiments, the poly(PD-co-HSA) copolymer particles have an average diameter of about 600 nm to about 800 nm. In some embodiments, the poly(PD-co-HSA) copolymer particles have an average diameter of about 600 nm.

The molecular weight of the poly(PD-co-HSA) copolymer can vary. For example, the average molecular weight of the poly(PD-co-HSA) copolymer can be about 500 g/mol to about 10000 g/mol. In some embodiments, the average molecular weight of the poly(PD-co-HSA) copolymer is about 500 g/mol, about 1000 g/mol, about 2000 g/mol, about 3000 g/mol, about 4000 g/mol, about 5000 g/mol, about 6000 g/mol, about 7000 g/mol, about 8000 g/mol, about 10000 g/mol, or a range between any two of these values.

The bulk electrical conductivity of the poly(PD-co-HSA) copolymer can also vary. For example, the poly(PD-co-HSA) copolymer particle can exhibit an intrinsically electrical conductivity of about $1 \times 10^{-9}$ S/cm to about 1 S/cm. In some embodiments, the poly(PD-co-HSA) copolymer particle can exhibit an intrinsically electrical conductivity of about $1 \times 10^{-9}$ S/cm, about $5 \times 10^{-8}$ S/cm, about $1 \times 10^{-8}$ S/cm, about $5 \times 10^{-7}$ S/cm, about $1 \times 10^{-7}$ S/cm, about $5 \times 10^{-6}$ S/cm, about $1 \times 10^{-6}$ S/cm, about $5 \times 10^{-5}$ S/cm, about $1 \times 10^{-5}$ S/cm, about $1 \times 10^{-4}$ S/cm, about $1 \times 10^{-3}$ S/cm, about $1 \times 10^{-2}$ S/cm, about 0.1 S/cm, about 1 S/cm, or a range between any two of these values. In some embodiments, the poly(PD-co-HSA) copolymer particles exhibit an average bulk electrical conductivity of about $1 \times 10^{-9}$ S/cm$^{-1}$ to about 1 S/cm$^{-1}$. In some embodiments, the poly(PD-co-HSA) copolymer particles have an average bulk electrical conductivity of about $0.5 \times 10^{-9}$ S/cm$^{-1}$.

Methods for Making Poly(PD-Co-HSA) Copolymers

Methods for making the poly(PD-co-HSA) copolymers are also enclosed herein. A non-limiting exemplary method include: forming a composition comprising at least one oxidizing agent, at least one optionally substituted 2-hydroxy-5-sulfonic aniline monomer, and at least one optionally substituted phenylenediamine monomer; and maintaining the composition under conditions effective to polymerize the 2-hydroxy-5-sulfonic aniline monomer and the optionally substituted phenylenediamine monomer to form the copolymer.

Various phenylenediamine can be used in the methods described herein. For example, optionally substituted m-phenylenediamine, optionally substituted p-phenylenediamine, optionally substituted o-phenylenediamine, or any combinations thereof can be used. In some embodiments, the optionally substituted phenylenediamine monomer is an optionally substituted m-phenylenediamine monomer. The optionally substituted m-phenylenediamine monomer can be, in some embodiments, represented by Formula VI:

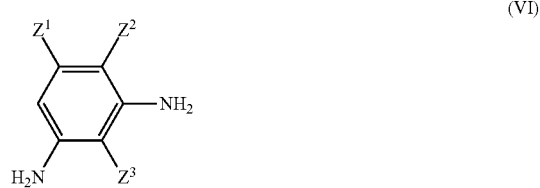

(VI)

wherein $Z^1$, $Z^2$ and $Z^3$ are as previously defined in the present disclosure. In some embodiments, $Z^1$ is hydrogen, —NH$_2$, —CH$_3$, —OH, —OCH$_3$, or —CH$_2$OH. In some embodiments, $Z^2$ is hydrogen, —OCH$_3$, or —SCH$_3$. In some embodiments, $Z^3$ is —OCH$_3$, hydrogen, or —CH$_3$. Examples of the optionally substituted m-phenylenediamine monomer include, but are not limited to,

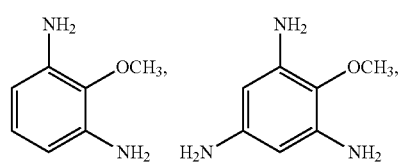

-continued

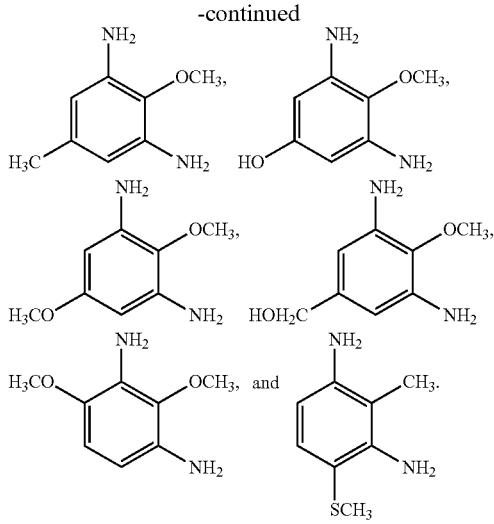

In some embodiments, the optionally substituted phenylenediamine monomer is an optionally substituted p-phenylenediamine monomer. The optionally substituted p-phenylenediamine can be, in some embodiments, represented by Formula VII:

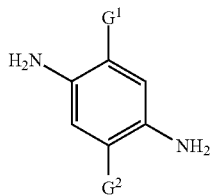

(VII)

wherein $G^1$ and $G^2$ are as previously defined in the present disclosure. In some embodiments, $G^1$ and $G^2$ are each independently hydrogen or methoxy. A non-limiting example of the optionally substituted p-phenylenediamine monomer is

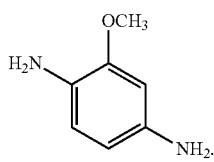

In some embodiments, the optionally substituted 2-hydroxy-5-sulfonic aniline monomer is represented by Formula VIII.

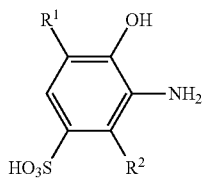

(VIII)

$R^1$ and $R^2$ are as previously defined in the present disclosure. In some embodiments, $R^1$ is hydrogen, $-CH_3$, $-NH_2$, or $-NHC(O)OCH_2CH_3$. In some embodiments, $R^2$ is hydrogen.

Examples of the optionally substituted 2-hydroxy-5-sulfonic aniline monomer includes, but are not limited to

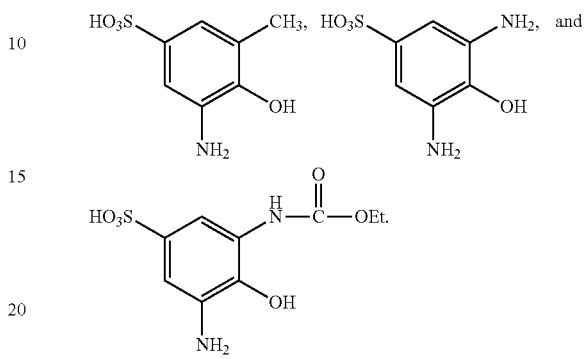

The steps and/or conditions for forming the poly(PD-co-HSA) copolymer are not particularly limited. Any suitable method of combining the ingredients can be employed. For example, the oxidizing agent can be combined (for example, mixed or dissolved) with a first solvent, and the optionally substituted 2-hydroxy-5-sulfonic aniline monomer and the optionally substituted phenylenediamine monomer can be combined (for example, mixed or dissolved) with a second solvent. The solution can then be combined by dropwise or continuous addition of one of the combined mixtures to the other. The first and second solvents can be the same or different. In some embodiments, the first solvent is at least partially immiscible in the second solvent. In some embodiments, the oxidizing agent is soluble in the first solvent. In some embodiments, the first solvent is distilled water. In some embodiments, both the optionally substituted 2-hydroxy-5-sulfonic aniline monomer and the optionally substituted phenylenediamine monomer are soluble in the second solvent. In some embodiments, the second solvent is an acid aqueous medium, for example an aqueous medium containing organic and/or inorganic acids. Examples of acids include, but are not limited to, HCl, $HNO_3$, $H_2SO_4$, $HClO_4$, $H_3PO_4$, $H_5IO_6$, $CH_3COOH$, HCOOH, HClO, $HClO_3$, and any combination thereof. The pH of the aqueous acid medium can be, for example, about 1 to about 6. In some embodiments, the pH of the aqueous acid medium is less than or equal to about 6, less than or equal to about 5, less than or equal to about 4, or less than or equal to about 3. As one example, the polymerization solvent can include a protonic acid, such as 1M HCl. And various pH modifying agents can be used to adjust and/or maintain the pH of the composition to a desired pH.

In some embodiments, forming the composition includes combining a first solution having a first solvent and the oxidizing agent; and a second solution having a second solvent, the optionally substituted 2-hydroxy-5-sulfonic aniline monomer, and the optionally substituted phenylenediamine monomer, wherein the optionally substituted 2-hydroxy-5-sulfonic aniline monomer and the optionally substituted phenylenediamine monomer are soluble in the first solvent and the second solvent. In some embodiments, the first solvent is an acidic aqueous medium. In some embodiments, the second solvent is an acidic aqueous medium.

Various oxidative agents can be used. Examples of the oxidizing agent include, but are not limited to, ammonium salts (such as ammonium persulfate), sodium persulfate, potassium persulfate, $CrO_3$, $K_2Cr_2O_7$, $K_2CrO_4$, $FeCl_3$, potassium iodate, $Na_3VO_4$, benzoyl peroxide (BPO), or combinations thereof. In some embodiments, the oxidizing agent is ammonium persulfate.

The molar ratio of the optionally substituted 2-hydroxy-5-sulfonic aniline monomer to the optionally substituted phenylenediamine monomer used to synthesize the poly(PD-co-HSA) copolymer can be modified, for example, to adjust the properties of the copolymer. The relative molar ratio of the optionally substituted 2-hydroxy-5-sulfonic aniline monomer to the optionally substituted phenylenediamine monomer in the composition can be, for example, about 1:99 to about 50:50. In some embodiments, the relative molar ratio of the optionally substituted 2-hydroxy-5-sulfonic aniline monomer to the optionally substituted phenylenediamine monomer is about 5:95 to about 10:90. In some embodiments, the relative molar ratio of the optionally substituted 2-hydroxy-5-sulfonic aniline monomer to the optionally substituted phenylenediamine monomer is about 5:95.

The molar ratio of the oxidizing agent to the monomer components (that is, the total of the optionally substituted 2-hydroxy-5-sulfonic aniline monomer and the optionally substituted phenylenediamine monomer) used to synthesize the poly(PD-co-HSA) copolymer can be modified, for example, to adjust the properties of the copolymer. The relative molar ratio of the oxidizing agent to the monomer components in the composition can be, for example, about 0.5:1 to about 3:1. In some embodiments, the relative molar ratio of the oxidizing agent to the monomer components is about 1:1.

After forming the composition having the at least one optionally substituted 2-hydroxy-5-sulfonic aniline monomer, at least one optionally substituted phenylenediamine monomer, and the oxidizing agent, the composition can be maintained at conditions effective to polymerize the monomer components to form the copolymer. For example, the composition can be maintained at about atmospheric pressure and a temperature of about 0° C. to about 100° C., for example, about 5° C. to about 50° C. In some embodiments, the temperature is about 5° C. to about 50° C. In some embodiments, the temperature is about 30° C.

The composition having the at least one optionally substituted 2-hydroxy-5-sulfonic aniline monomer, at least one optionally substituted phenylenediamine monomer, and the oxidizing agent can be maintained at the conditions for a period of time sufficient to obtain the copolymer. The composition, for example, can be maintained at the conditions for about 6 hours to about a week. In some embodiments, the composition is maintained at the conditions for about 6 hours to about 48 hours. In some embodiments, the composition is maintained at the conditions for about 24 hours.

The poly(PD-co-HSA) copolymer can, in some embodiments, be isolated from the composition by centrifuging the composition to obtain one or more copolymers within the precipitate. The copolymer can be subject to various other optional treatments, such as washing, doping, dedoping, and the like.

The yield of the copolymer using the method will vary depending upon various factors, such as the temperature and the like. For example, the yield of the copolymer can be about 50% to about 99.9% by weight of the copolymer relative to a total amount of the monomer components in the composition. In some embodiments, the method yields at least about 50%, at least about 60%, at least about 70%, at least about 80%, at least about 90%, or at least about 95% by weight of the copolymer relative to a total amount of the monomer components in the composition.

Compositions Including a Polymer Matrix and Lead-Ion-Selective Ionophores

Also provided herein are compositions including a polymer matrix and one or more ionophores that are selective toward lead ions. In some embodiments, the lead-ion-selective ionophore includes one or more poly(PD-co-HSA) copolymers, for example any of the poly(PD-co-HSA) copolymers disclosed herein.

The polymer matrix can include various polymer component, for example, one or more vinyl polymers, polyacrylate, silicone rubber, polyurethane, or any combination thereof. As used herein, vinyl polymers are polymers derived from vinyl monomers. Examples of vinyl polymers include, but are not limited to, ethylene-vinyl acetate copolymer (EVA), polyvinyl fluoride (PVF), polyvinyl acetate (PVAc), PVA (polyvinyl alcohol), polyvinylidene fluoride (PVDF), polyvinylidene chloride (PVDC); polytetrafluoroethylene (PTFE), copolymers of vinyl chloride, and any combinations thereof.

In some embodiments, the polymer matrix include ethylene-vinyl acetate copolymer (EVA). The amount of the ethylene monomer unit and the vinyl acetate unit in EVA can vary, for example, to adjust the properties of the EVA. For example, the EVA can have vinyl acetate monomer unit in an amount of about 5% to about 90%. In some embodiments, the EVA have vinyl acetate monomer unit in an amount of about 5%, about 10%, about 20%, about 30%, about 40%, about 50%, about 60%, about 70%, about 80%, about 90%, or a range between any two of these values, by weight. In some embodiments, the EVA has vinyl acetate monomer unit in an amount of about 40% to about 80% by weight. In some embodiments, the EVA has vinyl acetate monomer unit in an amount of about 40% by weight.

The polymer matrix can be substantially plasticizer free. For example, the polymer matrix can contain substantially plasticizer-free EVA. The polymer matrix can contain, for example, about 20% to about 95% of EVA by weight. In some embodiments, the polymer matrix can contain about 20%, about 30%, about 40%, about 50%, about 60%, about 70%, about 80%, about 90%, about 95%, or a range between any two of these values, EVA by weight. In some embodiments, the polymer matrix contains at least about 95% of EVA by weight. Examples of plasticizer include, but are not limited to, phthalate-based plasticizers. Non-limiting examples of phthalate-based plasticizers include di(2-ethylhexyl) phthalate (DEHP), diisononyl phthalate (DINP), di-n-butyl phthalate (DBP), benzyl butyl phthalate (BBP), diisodecyl phthalate (DIDP), di(n-octyl) phthalate (DNOP), diisooctyl phthalate (DIOP), diethyl phthalate (DEP), diisobutyl phthalate (DIBP), dimethyl phthalate (DMP), diallyl phthalate (DAP), di-n-propyl phthalate (DPP), butyl cyclohexyl phthalate (BCP), di-n-pentyl phthalate (DNPP), dicyclohexyl phthalate (DCP), di-n-hexyl phthalate (DNHP), diisohexyl phthalate (DIHxP), diisoheptyl phthalate (DIHpP), butyl decyl phthalate (BDP), n-Octyl n-decyl phthalate (ODP), di(2-Propyl Heptyl) phthalate (DPHP), diundecyl phthalate (DUP), diisoundecyl phthalate (DIUP), diisoundecyl phthalate (DTDP), diisotridecyl phthalate (DIUP), 1,2-benzenedicarboxylic acid esters, and combinations thereof.

The polymer matrix can contain various amount of plasticizer(s). For example, the polymer matrix can contain about 0% wt % to about 1 wt % plasticizer(s) based on the total weight of the polymer matrix. In some embodiments, the polymer matrix contains less than about 0.01 wt %, less than about 0.05 wt %, less than about 0.1 wt %, less than about 0.5 wt %, less than about 0.6 wt %, less than about 0.7 wt %, less than about 0.8 wt %, less than about 0.9 wt %, or less than about 1 wt % plasticizer(s) based on the total weight of the polymer matrix.

In some embodiments, the composition includes one or more poly(PD-co-HSA) copolymers and a polymer matrix containing one or more vinyl polymers, for example one or more of the vinyl polymer disclosed herein. In some embodiments, the composition includes one or more poly (PD-co-HSA) copolymers and a polymer matrix containing a vinyl polymer, polyacrylate, silicone rubber, polyurethane, or any combinations thereof. In some embodiments, the composition includes one or more poly(PD-co-HSA) copolymers and a polymer matrix containing EVA.

In some embodiments, the composition includes one or more ionophores that are selective toward lead ions and EVA polymer. In some embodiments, the composition includes one or more poly(PD-co-HSA) copolymers and EVA polymer.

The amount of the ionophores, for example the poly(PD-co-HSA) copolymers, present in the composition is not particularly limited and can vary. For example, the composition can have about 0.1% to about 10% the ionophores by weight. In some embodiments, the composition has about 0.1%, about 0.5%, about 1%, about 2%, about 3%, about 4%, about 5%, about 6%, about 7%, about 8%, about 9%, about 10%, or a range between any two of these values, the ionophores by weight. In some embodiments, the composition has about 0.1% to about 10% the ionophores (for example, any of the poly(PD-co-HSA) copolymers disclosed herein) by weight. In some embodiments, the composition has about 1% to about 3% the ionophores (for example, any of the poly(PD-co-HSA) copolymers disclosed herein) by weight. In some embodiments, the composition has about 4.5% the ionophores (for example, any of the poly(PD-co-HSA) copolymers disclosed herein) by weight.

In addition to the vinyl polymer and the ionophores (for example, poly(PD-co-HSA) copolymers), the composition disclosed herein can also contain other components, including but not limited to, one or more ion exchangers. Non-limiting examples of exchangers include sodium tetraphenylborate (NaTPB), potassium tetraphenylborate (KTPB), potassium tetrakis(4-chlorophenyl)]borate (KTClPB), potassium tetrakis[3,5-bis(trifluoromethyl)phenyl]borate (KTFPB), sodium tetrakis[3,5-bis(trifluoromethyl)phenyl] borate (NaTFPB), and any combinations thereof. The amount of the ion exchangers present in the composition can vary. For example, the composition can have about 0% to about 10% of the ion exchanger by weight. In some embodiments, the composition has about 0%, about 0.1%, about 0.5%, about 1%, about 2%, about 3%, about 4%, about 5%, about 6%, about 7%, about 8%, about 9%, about 10%, or a range between any two of these values, the ion exchanger by weight. In some embodiments, the composition does not contain ion exchangers. In some embodiments, the composition has about 1% to about 3% the ion exchangers by weight. In some embodiments, the composition has about 4.5% the ion exchangers by weight.

Composition disclosed herein can also contain components, including but not limited to, one or more electrical conducting additives. Examples of electrical conducting additive include, but are not limited to, conducting polymers, metal nanoparticles, graphene nanosheets, carbon nanotubes, carbon black, and any combinations thereof. A conducting polymer can include, for example, polyaniline, polypyrrole, polythiophene, polyacetylene, poly(3,4-ethylenedioxythiophene), poly(3-octylthiophene), or any combination thereof. In some embodiments, the electrical conducting additive comprises polyaniline nanosticks.

The composition including a polymer matrix and one or more ionophores that are selective toward lead ions can be substantially plasticizer free. For example, the composition contains about 0 wt % to about 1.5 wt % plasticizer(s) based on the total weight of the composition. In some embodiments, the composition contains less than about 0.01 wt %, less than about 0.05 wt %, less than about 0.1 wt %, less than about 0.5 wt %, less than about 0.6 wt %, less than about 0.7 wt %, less than about 0.8 wt %, less than about 0.9 wt %, less than about 1 wt %, or less than about 1.5 wt % plasticizer(s) based on the total weight of the composition.

The composition can, in some embodiments, be in the form of a liquid that includes the ionophores (for example, the poly(PD-co-HSA) copolymers described herein) and the polymer matrix described herein. For example, the composition can be dispersed or dissolved in a solvent. The solvent can be an organic solvent or water. The organic solvent can, for example, be a non-polar solvent, a polar aprotic solvent, a polar protic solvent, or combinations thereof. In some embodiments, the composition includes a polar aprotic solvent. Non-limiting examples of polar aprotic solvents include n-methyl-2-pyrrolidone (NMP), dimethylformamide (DMF), dimethyl sulfoxide (DMSO), and tetrahydrofuran (THF).

The composition can, in some embodiments, be in the form of a solid that includes the ionophores (for example, the poly(PD-co-HSA) copolymers described herein) and the polymer matrix described herein. In some embodiments, a solid form of the copolymer can be obtained by precipitating or drying the composition from solution (for example, solvent casting).

The composition can be in various forms, including but not limited to, the form of a film, a membrane, a foil, and any combinations thereof. In some embodiments, the composition forms a polymeric membrane. The thickness of the polymeric membrane can vary. For example, the polymeric membrane can have an average thickness of about 10 µm to about 1000 µm. In some embodiments, the polymeric membrane has an average thickness of about 10 µm, about 20 µm, about 30 µm, about 50 µm, about 100 µm, about 200 µm, about 300 µm, about 400 µm, about 500 µm, about 600 µm, about 700 µm, about 800 µm, about 900 µm, about 1000 µm, or a range between any two of these values. In some embodiments, the polymeric membrane has an average thickness of about 30 µm to about 400 µm. The polymeric membrane can be used, in some embodiments, for ion selective measurement. The ion selective measurement can be a potentiometric measurement. The polymeric membrane is, in some embodiments, substantially plasticizer free. In some embodiments, the polymeric membrane is used as a sensing membrane for detecting Pb(II) in a sample.

The polymeric membranes as described herein are long-lasting. For example, the operation lifetime of the polymeric membrane for ion selective measurement can be about 3 weeks to about 30 weeks. In some embodiments, the operation lifetime of the polymeric membrane for ion selective measurement is more than about 3 weeks, more than about 5 weeks, more than about 8 weeks, more than about 10 weeks, more than about 12 weeks, more than about 16 weeks, more than about 20 weeks, more than 25 weeks, or more than 30 weeks.

The method for making the polymeric membrane is also provided herein. The method can include: forming a composition comprising a polymer matrix and one or more ionophores that are selective toward lead ions; maintaining the composition under conditions effective to form a polymeric composition; and casting the polymeric composition to a solid surface to form a polymeric membrane. The ionophores can be any of the poly(PD-co-HSA) copolymers described herein. In some embodiments, the polymer matrix comprises one or more vinyl polymers, polyacrylate, silicone rubber, polyurethane, or any combination thereof. The composition can include one or more ion exchangers. In some embodiment, the composition includes one or more electrical conducting additives.

Apparatuses for Detecting Lead Ions

Ion Selective Electrodes (ISEs)

Also enclosed herein are Pb(II) ion selective electrodes (Pb(II) ISEs) that contain the polymeric membrane described herein.

FIG. 1 depicts an illustrative embodiment of a Pb(II) ISE. The Pb(II)-ISE 100 can include sensing membrane 110, internal reference electrode 120, supporting tube 130, internal electrolyte solution 140, cap 150, and conductor wire 160. The internal reference electrode 120 is in contact with internal electrolyte solution 140 encapsulated in supporting tube 130. The sensing membrane 110 can be immersed into a sample suspected of containing one or more lead ions. Sensing membrane 110 can include a polymer matrix and any of the poly(PD-co-HSA) copolymer described herein. Sensing membrane 110 can include any one or more of the polymeric membranes disclosed herein. Sensing membrane 110 can also include EVA polymer and one or more lead-ion-selective ionophores (for example any of the poly(PD-co-HSA) copolymers described herein).

The Pb(II) ISE, in some embodiments, is used in conjunction with an external reference electrode to detect the presence and/or measure the concentration of lead ions in the sample. In some embodiments, both the Pb(II) ISE and the external reference electrode are contacted with the sample suspected of containing one or more lead ions to detect the presence of lead ions in the sample. The potential difference between the Pb(II) ISE and external reference electrode is, in some embodiments, a function of the concentration of lead ions in the sample.

In some embodiments, the external reference electrode is an electrode which has a stable and well-known electrode potential. In some embodiment, the external reference electrode has an internal half-cell supported in a tube containing a salt solution, the tube of salt solution being known as a salt bridge (also known as a bridge electrolyte solution). The salt bridge solution can be a concentrated equitransferent salt solution (for example, potassium chloride and potassium nitrate). Various electrode can be used as the external reference electrode, including but not limited, to saturated calomel electrode (SCE, $Hg/Hg_2Cl_2$), silver-silver chloride electrode (Ag/AgCl), and copper-copper(II) sulfate electrode.

In some embodiments, the Pb(II) ISE and the external reference electrode are attached to an ion meter (for example, a pH meter), where the ion meter can be used to detect an electromotive force (EMF) between the Pb(II) ISE and the external reference electrode. In some embodiments, the EMF value is proportional to the Pb(II) concentration in the sample to which the electrodes are exposed.

The operating lifetime of the polymeric sensing membrane can vary. For example, the polymeric sensing membrane can have an operating lifetime of about 3 weeks to about 30 weeks. In some embodiments, the polymeric sensing membrane has an operating lifetime of about 3 weeks, about 6 weeks, about 9 weeks, about 12 weeks, about 13 weeks, about 14 weeks, about 15 weeks, about 16 weeks, about 17 weeks, about 18 weeks, about 20 weeks, about 25 weeks, about 30 weeks, or a range between any two of these values. In some embodiments, the polymeric sensing membrane can have an operating lifetime of more than about 4 weeks, more than about 8 weeks, more than about 10 weeks, more than about 12 weeks, more than about 14 weeks, or more than about 16 weeks. In some embodiments, the polymeric sensing membrane has an operating lifetime of more than about 10 weeks. In some embodiments, the polymeric sensing membrane has an operating lifetime of more than about 16 weeks.

Also disclosed herein are sensors for measuring lead ions. The sensor can include the lead ion-selective electrode disclosed herein. In some embodiments, the sensor includes a lead ion-selective electrode, where the lead ion-selective electrode includes a polymer matrix and one or more poly(PD-co-HSA) copolymers. In some embodiments, the sensor further includes a reference electrode.

Methods for Detecting Lead Ions

Some embodiments disclosed herein include methods for detecting the presence and/or the concentration of lead ions (sometimes written as Pb (II) or $Pb^{2+}$), in a sample.

In some embodiments, the method include providing a sample suspected of containing one or more lead ions; contacting the sample with a sensor, where the sensor includes a reference electrode and a lead ion-selective electrode, where the lead ion-selective electrode comprises a polymer matrix and one or more ionophores selective for lead ions; and measuring an electromotive force (EMF) between the reference electrode and the lead ion-selective electrode. In some embodiments, the polymer matrix includes one or more EVA polymers. In some embodiments, the one or more ionophores selective for lead ions include one or more poly(PD-co-HSA) copolymers, for example one or more of the poly(PD-co-HSA) copolymers described herein. In some embodiments, the sample is contacted with the lead ion-selective electrode. In some embodiments, the sample is contacted with the reference electrode and the lead ion-selective electrode.

The methods can be used for detecting the presence of lead ions and measuring the amount and/or concentration of lead ions in a sample. In some embodiments, the sensor is a potentiometric sensor which functions substantially logarithmic. In some embodiments, the ion sensitive measurement is a potentiometric measurement. In some embodiments, the amount and/or the concentration of the lead ions in the sample correlate with the EMF measured. In some embodiments, the amount and/or the concentration of the lead ions in the sample positively correlate with the EMF measured. In some embodiments, the relation between the concentration of lead ions and the EMF measured is logarithmic. In some embodiments, the measured EMF is greater in the presence of lead ions than in the absence of lead ions.

The methods can be used for detecting the presence and/or concentration of Pb(II) in various types of samples. In some embodiments, the sample is an aqueous sample. In some embodiments, the sample is an environmental sample, a food product, a medicine product, a dietary supplement, a dental hygienic composition, a cosmetic product, a biological sample, or any combinations thereof. Examples of environmental sample include, but are not limited to, river water, rainwater, waste water, and any combinations thereof. In some embodiments, the sample is tap water. In some embodiments, the sample is a food product or a medicine product. In some embodiments, the food product is a beverage. In some embodiments, the sample is a clinical sample or body fluid, for example, a urine sample or a blood sample.

The concentration of lead ions in the sample can vary. For example, the concentration of the lead ions in the sample can be about $10^{-9}$ mol/L (i.e., $10^{-9}$ M) to about 0.1 M. In some embodiments, the concentration of the lead ions in the sample is about $10^{-9}$ M, about $5 \times 10^{-9}$ M, about $10^{-8}$ M, about $5 \times 10^{-8}$ M, about $10^{-7}$ M, about $5 \times 10^{-7}$ M, about $10^{-6}$ M, about $5 \times 10^{-6}$ M, about $10^{-5}$ M, about $5 \times 10^{-5}$ M, about $10^{-4}$ M, about $5 \times 10^{-4}$ M, about $10^{-3}$ M, about $5 \times 10^{-3}$ M, about $10^{-2}$ M, about $5 \times 10^{-2}$ M, about 0.1 M, and a range between any two of these values. In some embodiments, the concentration of the lead iron in the sample is about $10^{-3}$ M to about $10^{-7}$ M. In some embodiments, the concentration of the lead ion is about $10^{-4}$ M to about $10^{-6}$ M. In some embodiments, the concentration of the lead ion in the sample is less than about $10^{-5}$ M.

The compositions and methods described herein can allow rapid detection of lead ions in a sample. For example, the minimal time needed for the sample to contact with the compositions, including the lead ion-selective electrodes disclosed herein, to allow detection of the lead ions and/or measuring of the concentration of the lead ions in the sample can be about 30 minutes to about 15 seconds. In some embodiments, the minimal time needed for the sample to contact with the compositions to allow detection of the lead ions and/or measuring of the concentration of the lead ions in the sample is about 30 minutes, about 20 minutes, about 10 minutes, about 9 minutes, about 8 minutes, about 7 minutes, about 6 minutes, about 5 minutes, about 4 minute, about 3 minutes, about 2 minutes, about 1 minutes, about 30 seconds, about 15 seconds, or a range between any two of these values. In some embodiments, the minimal time needed for the sample to contact with the compositions to allow detection of the lead ions and/or measuring of the concentration of the lead ions in the sample is at most about 5 minutes, at most about 2 minutes, at most about 60 seconds, or at most about 30 seconds.

EXAMPLES

Additional embodiments are disclosed in further detail in the following examples, which are not in any way intended to limit the scope of the claims.

Example 1

Polymerization of Poly(mPD-Co-HSA) Copolymer

The chemical oxidative copolymerization of m-phenylenediamine (mPD) and 2-hydroxy-5-sulfonic aniline (HSA) for the synthesis of poly(mPD-co-HSA) copolymer particles was carried out in a synthesis procedure described below.

A preparation procedure of the poly(mPD-co-HSA) copolymer particles include mixing mPD (2.055 g, 19 mmol) and HSA (0.211 g, 1 mmol) in a glass flask which contains 75 mL of 1.0 M HCl to prepare a co-monomer solution. Ammonium persulfate (4.564 g, 20 mmol) was dissolved separately in 25 mL of 1.0 M HCl to prepare an oxidant solution. Both of the co-monomer solution and oxidant solution were put into a water bath at 30° C. for over 30 minutes. The co-monomer solution was stirred and treated with the oxidant solution dropwise at a rate of one drop (60 µL) every 3 seconds over 30 minutes at 30° C. The reaction mixture was constantly magnetically-stirred in the 30° C. water bath for 24 hours and the resulting polymer microparticles were centrifuged and rinsed thoroughly with distilled water to remove the residual oxidant, water-soluble oligomer, and other possible by-products. The resulting black solid powders of as-prepared copolymer salts were left to dry in air at 50° C. for 3 days. The possible copolymerization reaction is shown in Scheme 1. In addition, bulk electrical conductivity of the polymer particle sheet was obtained according to its thickness and resistance measured with UNI-TUT70A multimeter.

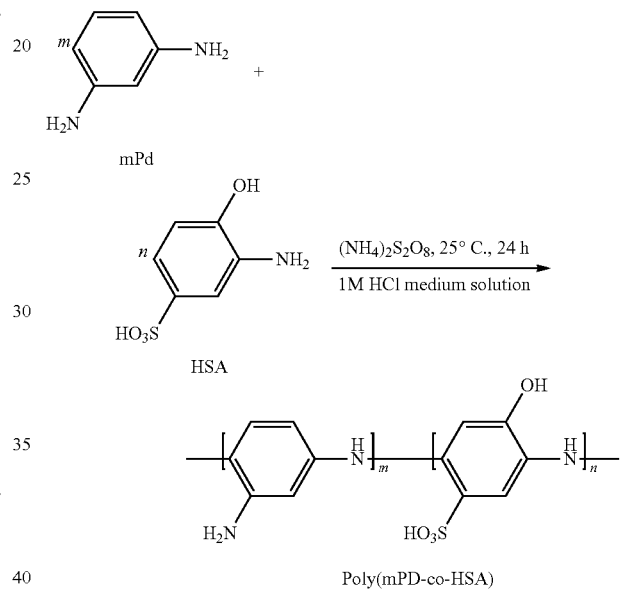

Scheme 1

Figure 2:
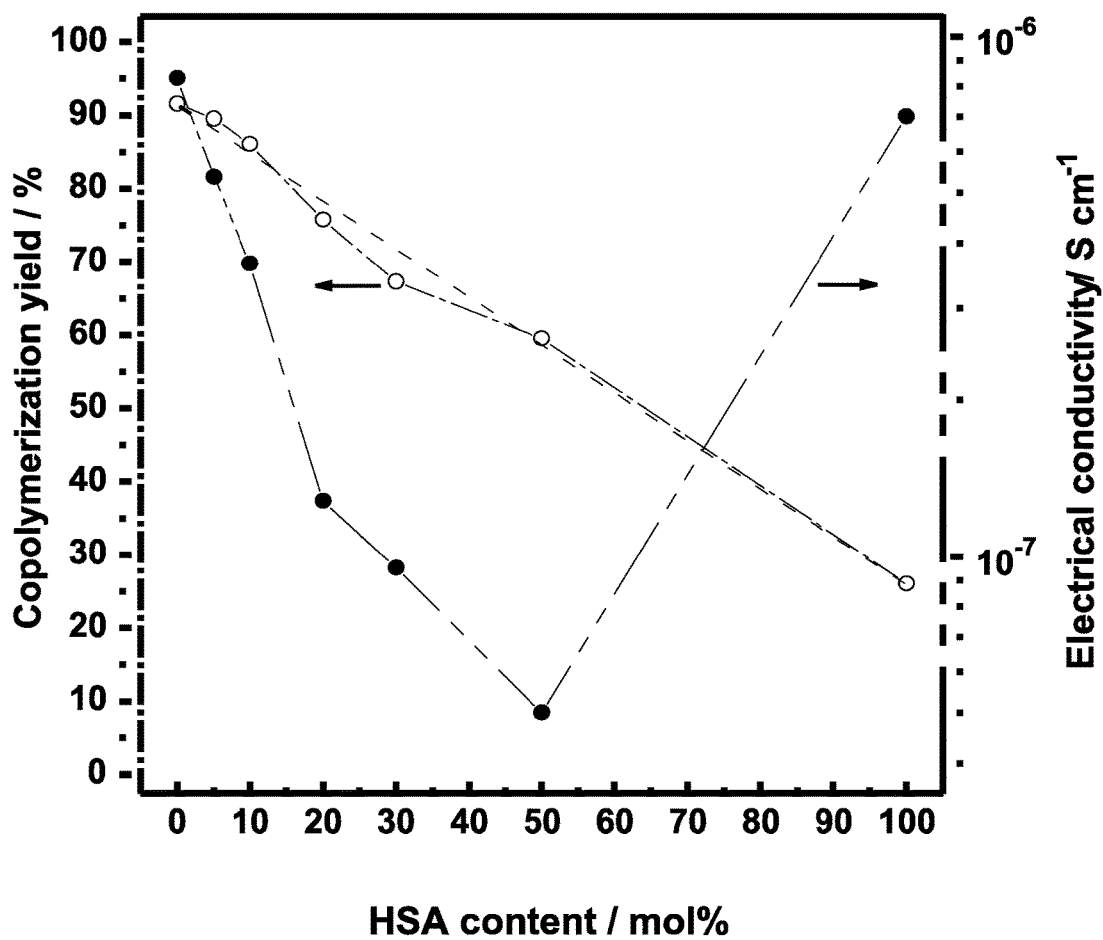
FIG. 2 is a graph showing variation of polymerization yield and electrical conductivity of poly(mPD-co-HSA) copolymer particles with various mPD/HSA molar ratios at an initial polymerization temperature of 30° C. for 24 hours. The left y-axis represents copolymerization yield (%) of the copolymer particles and the right y-axis represents electrical conductivity (S cm$^{-1}$) of the copolymer particles. The even dashed line represents a simple addition of two homopolymer yields.

As show in FIG. 2, the polymerization yield decreased monotonically from 91.6 to 26.0% with increasing HSA content from 0 to 100%, suggesting that more HSA monomers would weaken the polymerization activity to some extent because of stronger steric hindrance and attracting electron effect, and water soluble tendency from sulfonic groups. Since HSA monomer and its homopolymer are water soluble, the HSA homopolymer can be obtained only when a non-aqueous precipitator like acetone was used instead of water. All other six polymer samples having mPD and HSA molar ratios from 100/0 to 50/50 have been purified or washed with water. It was determined that the copolymerization between mPD and HSA indeed occurred because the electrical conductivity of the polymers non-monotonically changes with HSA contents, for example, decreases first and then increases, giving a minimum conductivity of $5.03 \times 10^{-8}$ S/cm at HSA content of 50 mol %, because the sulfonic and hydroxyl groups introduced into mPD units can cause a torsion of the copolymer backbones, thereby shortening the conjugation length. Furthermore, HSA homopolymer showed slightly lower conductivity than mPD homopolymer but much higher conductivity than mPD/HSA (50/50) copolymer. Without being bound by any specific theory, it is believed that differences between HSA homopolymer and mPD homopolymer, HSA homopolymer and mPD/HSA (50/50) copolymer are possibly due to higher chain structure regularity and thus better self-doping effect than the copolymers.

The mPD/HSA (50/50) copolymerization was also semi-quantitatively confirmed by the yield of up to 59.5% that is higher than 50%. At least 9.5 mol % HSA units have been incorporated into the polymer chains, forming copolymer chains. Otherwise, all HSA homopolymer should be washed away from the final products by water. Assuming that copolymerization follows a simple addition of two homopolymer yields of 91.6 and 26.0 for mPD and HSA co-monomers respectively, as predicted by the dashed line in FIG. 2, the copolymerization yield would be 58.8%. However, higher actual yield of 59.5% signifies that copolymerization does happen between mPD and HSA co-monomers. The polymerization at other co-monomer ratios from 95/5 to 90/10 is slightly positive copolymerization effect but negative copolymerization effect at the co-monomer ratios from 80/20 to 70/30.

This example shows that poly(mPD-co-HSA) copolymer has been obtained using the preparation procedure described above.

Example 2

Measurements of Poly(mPD-Co-HSA) Copolymer Particles poly(mPD-co-HSA) copolymer particles were prepared using the procedures described in Example 1. Macromolecular and supramolecular structures of the copolymer particles were determined in this example.

UV-Vis Spectra

Figure 3A:
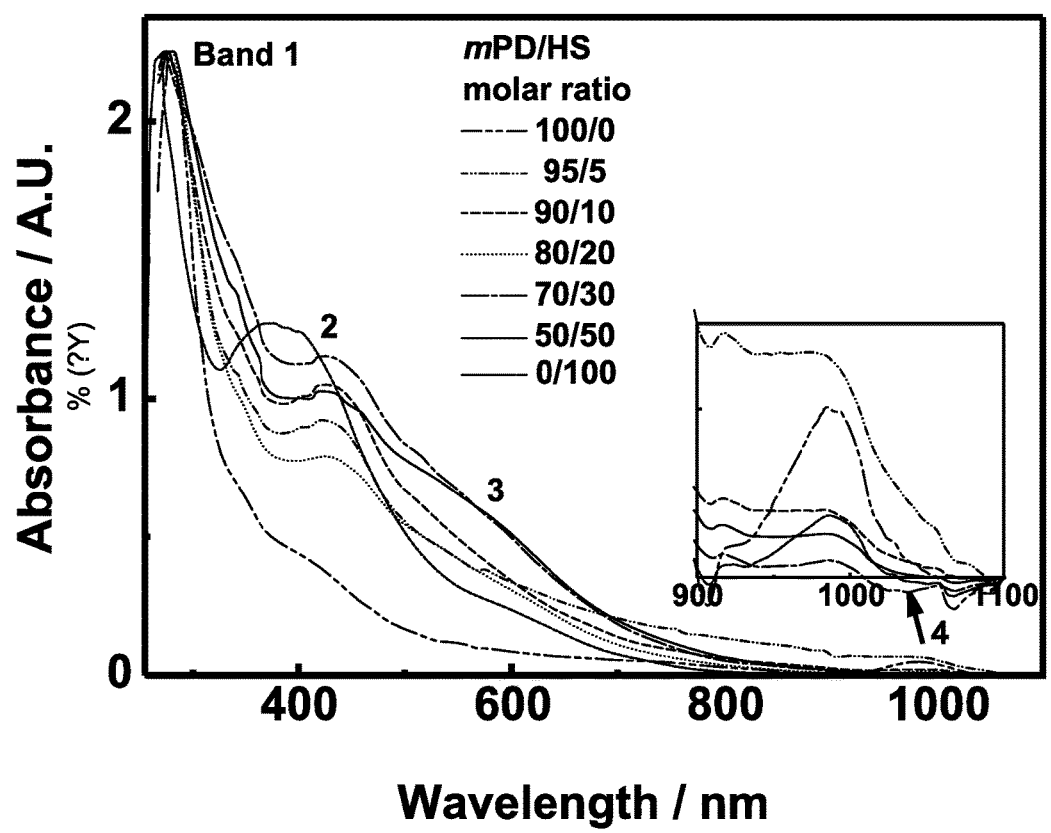
FIGS. 3A and 3B show (A) UV-vis spectra in DMSO and (B) FT-IR spectra of poly(mPD-co-HSA) copolymer particles with various mPD/HSA molar ratios.
Figure 3B:
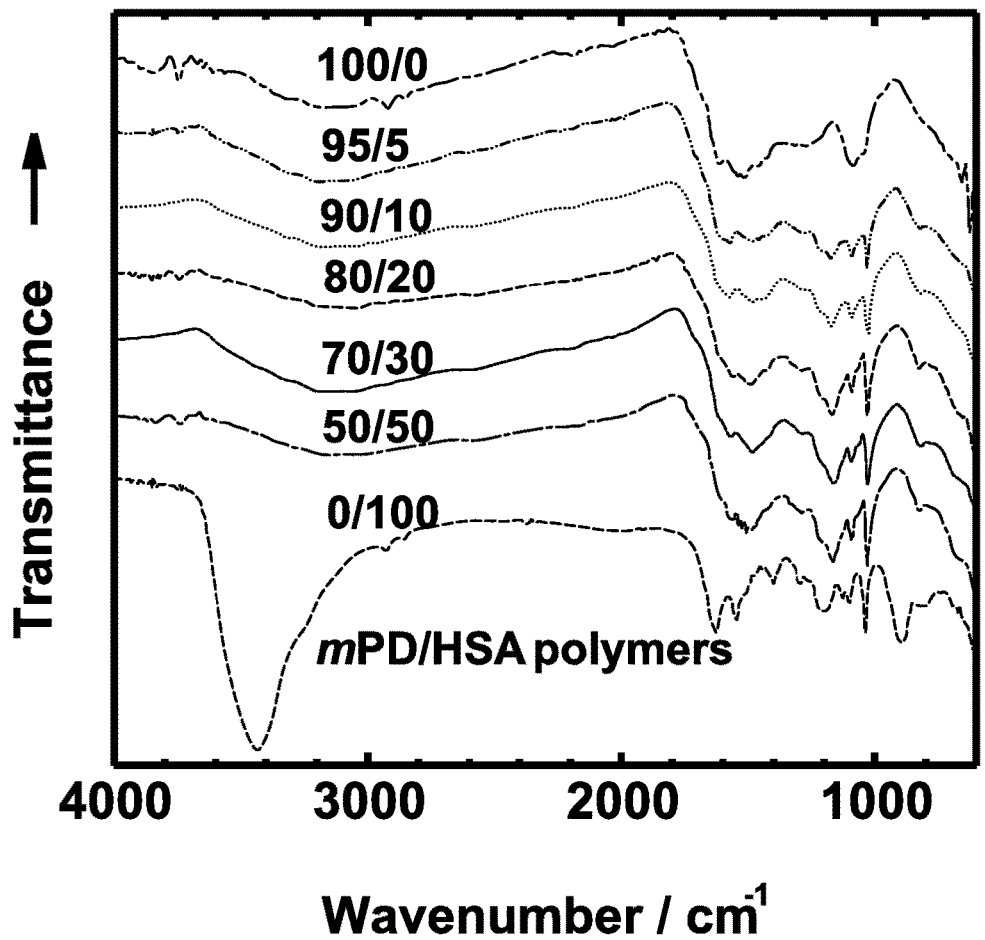

UV-vis spectra of the poly(mPD-co-HSA) copolymer particles were recorded by UV765CRT (Shanghai Jing-ke Instruments Factory, China). UV-vis absorption spectra of the copolymer salts in DMSO (FIG. 3A) show four characteristic bands: the strongest band 1 around 265-285 nm due to $\pi$-$\pi$* transition of all aromatic rings in copolymer chains, which has a blue shift compared with the aniline/sulfonic aniline copolymer; the weak band 3 in a long wavelength range of 550-650 nm due to $\pi$-$\pi$* excitation of benzenoid to the quinoid ring in the polymer chains; the medium band 2 at 370-450 nm mainly due to HSA units in the copolymers because only a very weak band 2 appears in the mPD homopolymer, an indication of the existence of the HSA units in the synthesized copolymer; the weakest band 4 at 910-1090 nm mainly due to mPD units in the copolymers because stronger band 4 appeared in the polymers containing more mPD units. There was no significant absorption in the UV-vis spectra of both monomers at a wavelength of longer than 350 nm, possibly indicating that a copolymerization indeed occurred between mPD and HSA co-monomers. Moreover, all five copolymers exhibited stronger band 3 in a wavelength range from 500 to 900 nm than two homopolymers, and particularly mPD/HSA (95/5) copolymer always has the strongest absorption in a wavelength range from 700 to 1090 nm. These two facts would suggest that the copolymers possessing more $\pi$-conjugated structure are achieved, which could be used to verify a positive copolymerization effect mentioned earlier IR Spectra IR spectra of the poly(mPD-co-HSA) copolymer particles were obtained by Nicolet FT-IR NEXUS-470 instrument. FIG. 3B shows the IR spectra of the microparticles of sevens representative copolymers. The broad and weak bands at 3188 and 3313 $cm^{-1}$ correspond to the N—H stretching of amine, imine, and/or O—H stretching. The mPD/HSA (95/5) copolymer demonstrates stronger band at 3100-3300 $cm^{-1}$ which could be evidence that there are more N—H and O—H groups in the copolymer than two homopolymers. The two absorptions at 1611 and 1489 $cm^{-1}$ are associated with the stretching of quinoid and benzenoid rings, respectively. It was revealed that there are more benzenoid rings in the mPD unit-containing copolymer than HSA homopolymer, but the mPD/HSA (95/5) copolymer was an exception. The weak absorption peak of C—N vibration in mPD units lies at 1289 $cm^{-1}$, which coincides with an earlier analysis. The stronger band at 1176 and 1214 $cm^{-1}$ are associated with the C—N stretching on the HSA units because HSA homopolymer also has two similar strong absorption, but the mPD homopolymer does not. Without being bound by any particular theory, it is believe that the sharpest absorption at 1031 $cm^{-1}$ may be related to the symmetric stretching vibration of the —$SO_3^-$ group on the HSA units. In summary, these adsorption bands indicate that the products obtained are not the mixture of the two homopolymers but indeed the true copolymers, because water-soluble HSA homopolymers have been removed completely.

Wide-Angle X-Ray Diffractograms

Figure 4A:
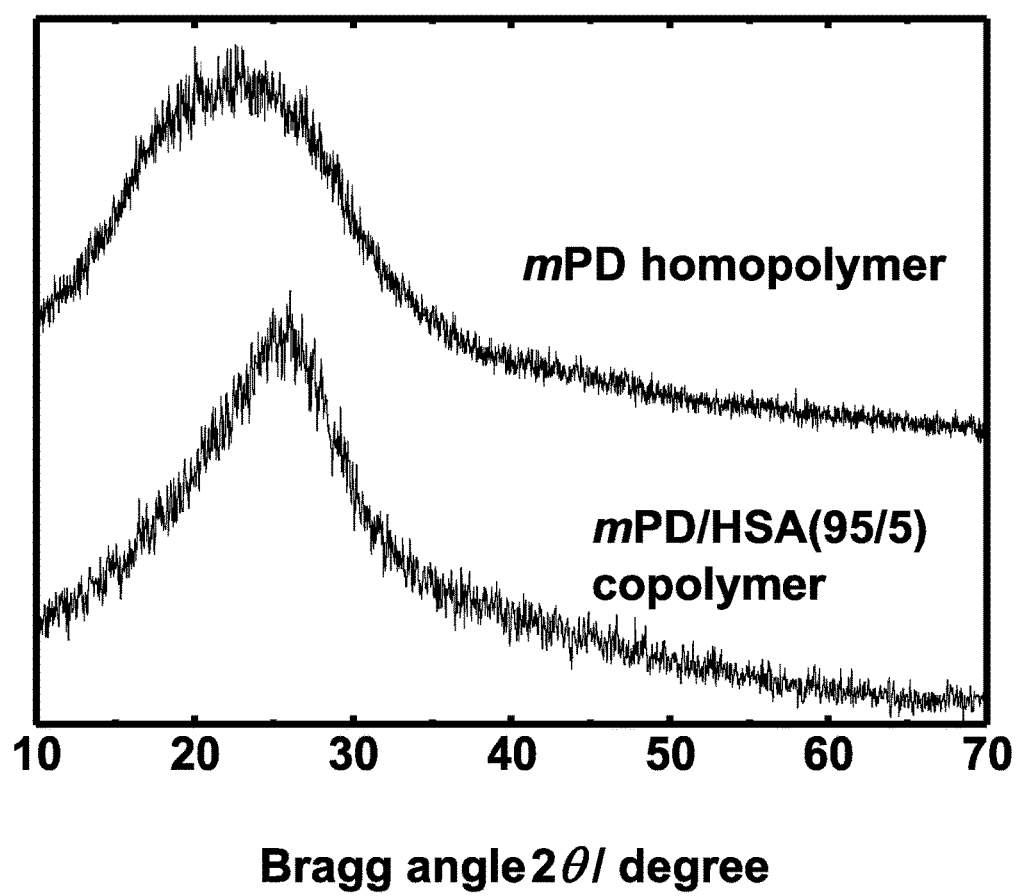
FIG. 4A shows wide-angle X-ray diffractograms of poly(mPD-co-HSA) particles with mPD/HSA molar ratios of 100/0 and 95/5 synthesized with $(NH_4)_2S_2O_8$/comonomer molar ratio of 1/1 in 1.0 M HCl at 30° C.

Wide-angle X-ray diffractograms of the poly(mPD-co-HSA) copolymer microparticles were recorded by Japan Rigaku D/max 2550 instrument. The wide-angle X-ray diffractograms of the particles of the mPD/HSA (95/5) copolymer and mPD homopolymer are shown in FIG. 4A, which present broad diffraction peaks in a Bragg angle range of 15°-35°, which is typical diffraction of amorphous polymers. These data suggests that the two polymer particles have amorphous structure characteristics, and the mPD homopolymer has the higher amorphous level. Such an amorphous structure should favor the penetration, interaction and then adsorption of heavy metal ions into the microparticles because the macromolecular chains in the amorphous states are relatively looser and more disordered than those in the crystalline states.

Example 3

Size and Morphology of Poly(mPD-Co-HSA) Copolymer Particles

Poly(mPD-co-HSA) copolymer particles were prepared using the procedures described in Example 1. Size and morphology of the copolymer particles were determined in this example.

Size and morphology of the copolymer particles were observed by a Jeol JSM-6340F field emission scanning electron microscope (FE-SEM) and FEI Tecnai F20-G2 FEGTEM high-resolution Transmission electron microscope (TEM). The samples for FE-SEM observation were dispersed by using ethanol on a silicon wafer and then subject to gold sputtering prior to observation. A dilute ethanol dispersion of the particle samples was ultrasonically prepared and dropped onto a copper grid covered with a carbon film to make a specimen for TEM observation. Particle size in water was analyzed by Beckman Coulter LS230 laser particle-size analyzer.

Figure 4B:
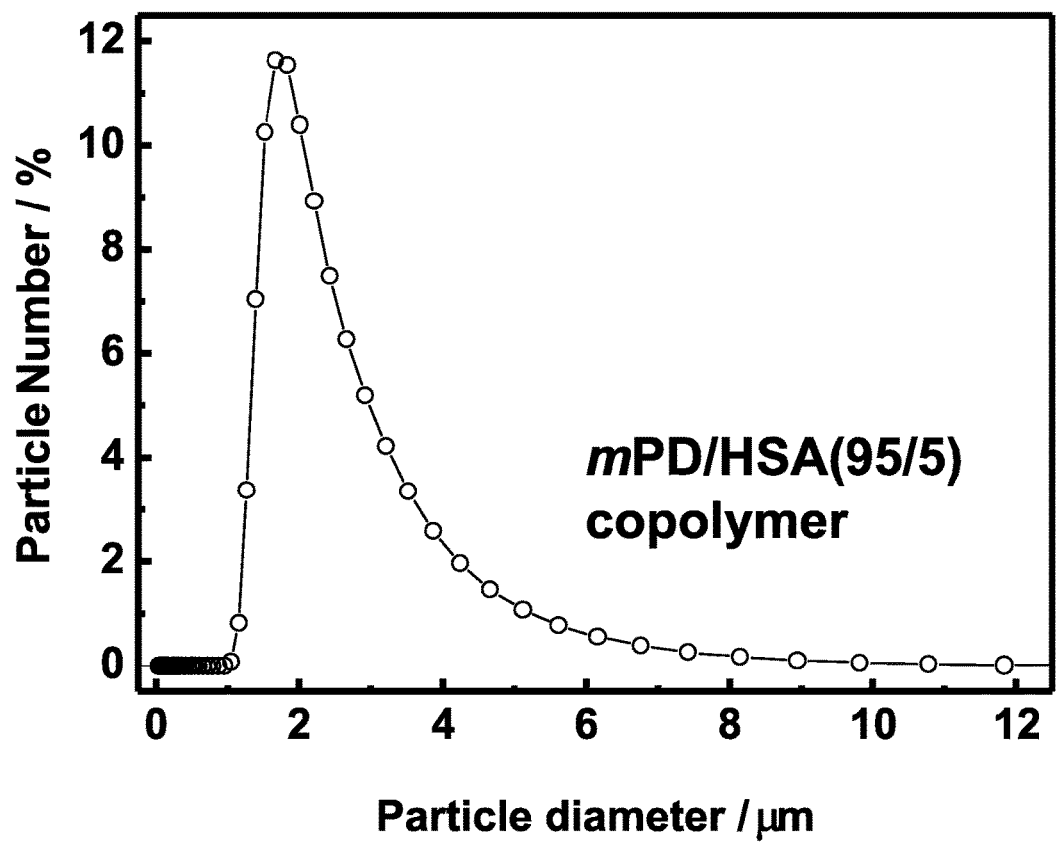
FIG. 4B is a plot showing size distribution of poly(mPD-co-HSA) particles with mPD/HSA molar ratios of 95/5 synthesized with $(NH_4)_2S_2O_8$/comonomer molar ratio of 1/1 in 1.0 M HCl at 30° C.
Figure 5:
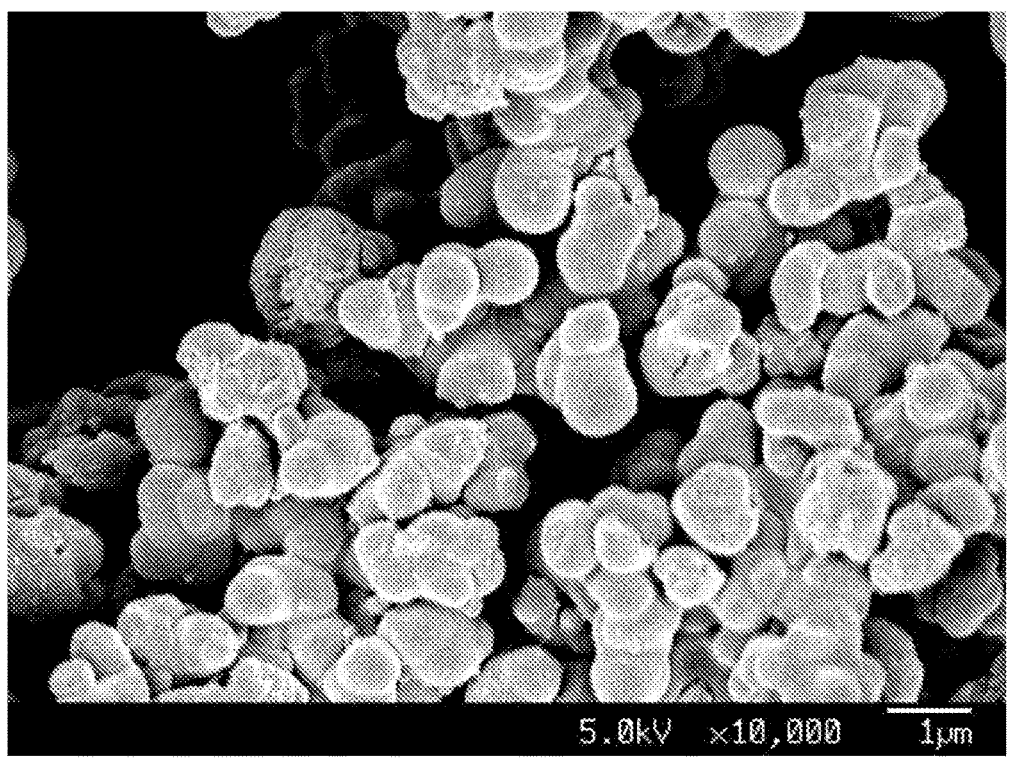
FIG. 5 is a scanning electron microscopy (SEM) image of mPD/HSA (95/5) copolymer particles synthesized under $(NH_4)_2S_2O_8$/comonomer molar ratio of 1/1 in 1.0 M HCl at 30° C.
Figure 6:
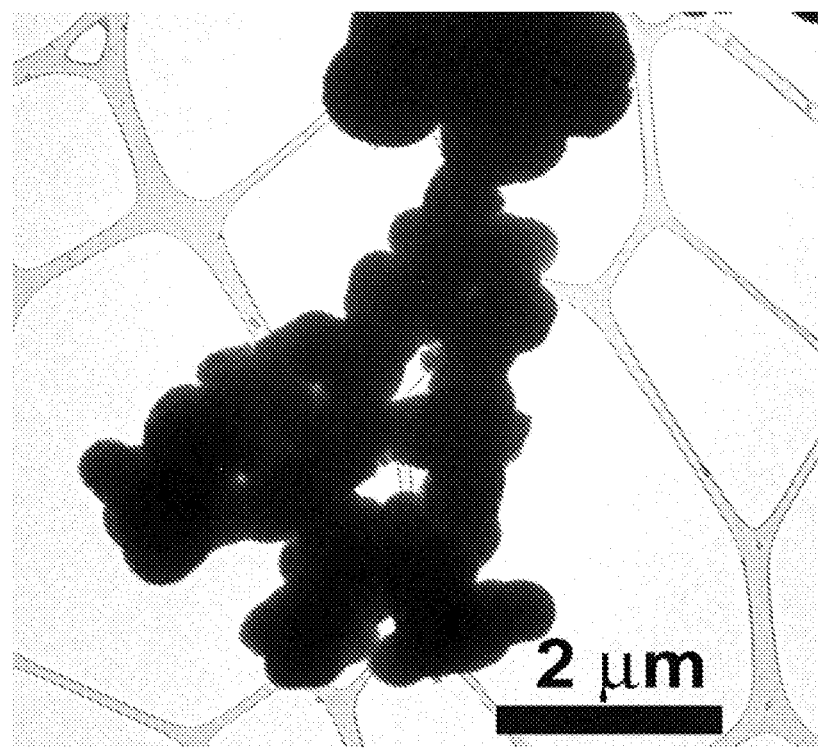
FIG. 6 is a field-emission TEM image of mPD/HSA (95/5) copolymer microparticles synthesized under a $(NH_4)_2S_2O_8$/comonomer molar ratio of 1/1 in 1.0 M HCl at 30° C.

Size distribution and morphology of the mPD/HSA (95/5) copolymer particles were analyzed, and the results are shown in FIGS. 4B, 5 and 6. The number-average diameter of the copolymer particles was found to be 2.44 μm which is smaller than that of the mPD homopolymer particles (3.16 μm). Without being bound by any specific theory, it is believe that the decline in the particle size in water media is attributed to the better water-dispersibility of the copolymer particles because of electrostatic repulsion of the negatively charged sulfonic and also hydroxyl groups on HSA units, which could efficiently stabilize the small particles with high surface energy. In addition, size polydispersity index of the copolymer particles is 2.16, which is slightly higher than that of the mPD homopolymer (1.17), indicating that the copolymer particles are generally uniform fine particles. Smaller fine particles are expected to result in more efficient interaction between the mPD/HSA (95/5) copolymer and Pb(II) ions.

Since the copolymer particles could agglomerate to some extent in water, the size of the copolymer particles determined by laser particle-size analysis was larger than that by SEM and TEM sometimes. SEM observation (FIG. 5) indicates that mPD/HSA copolymer particles aggregate into large particles to some extent regardless of ethanol dispersion, but some particles dispersed well and showed an average diameter of down to 500 nm, 700 nm, 900 nm, 1600 nm, 2000 nm, and 1100 nm for the mPD/HSA copolymer particles of 100/0, 95/5, 90/10, 80/20, 70/30, and 50/50, respectively. The elementary particles of the mPD/HSA (100/0) polymer, for example, mPD homopolymer, were found to be the smallest, but their dispersion was found to be the worst. mPD/HSA (95/5) copolymer particles were found to have the second smallest size and the best dispersion among all the mPD/HSA copolymer particles observed. Field-emission TEM images shown in FIG. 6 further confirmed that the mPD/HSA (95/5) copolymer particles are smaller than mPD/HSA (70/30) copolymer particles, having the average diameters of 600 and 800 nm, respectively. Moreover, the copolymer was found to be a loose aggregate having spheric and non-porous particles. Such a morphological feature of the mPD/HSA copolymer particles is believed to be favorable to interaction or complexation between the copolymer chains and lead(II) ions when using the copolymer particles as an ionophore in Pb(II) sensors.

Example 4

Complexation of Poly(mPD-Co-HSA) Copolymer with Lead Ions

Poly(mPD-co-HSA) copolymer particles were prepared using the procedures described in Example 1. Complexation of the copolymer particles with lead ions was determined in this example.

Figure 7:
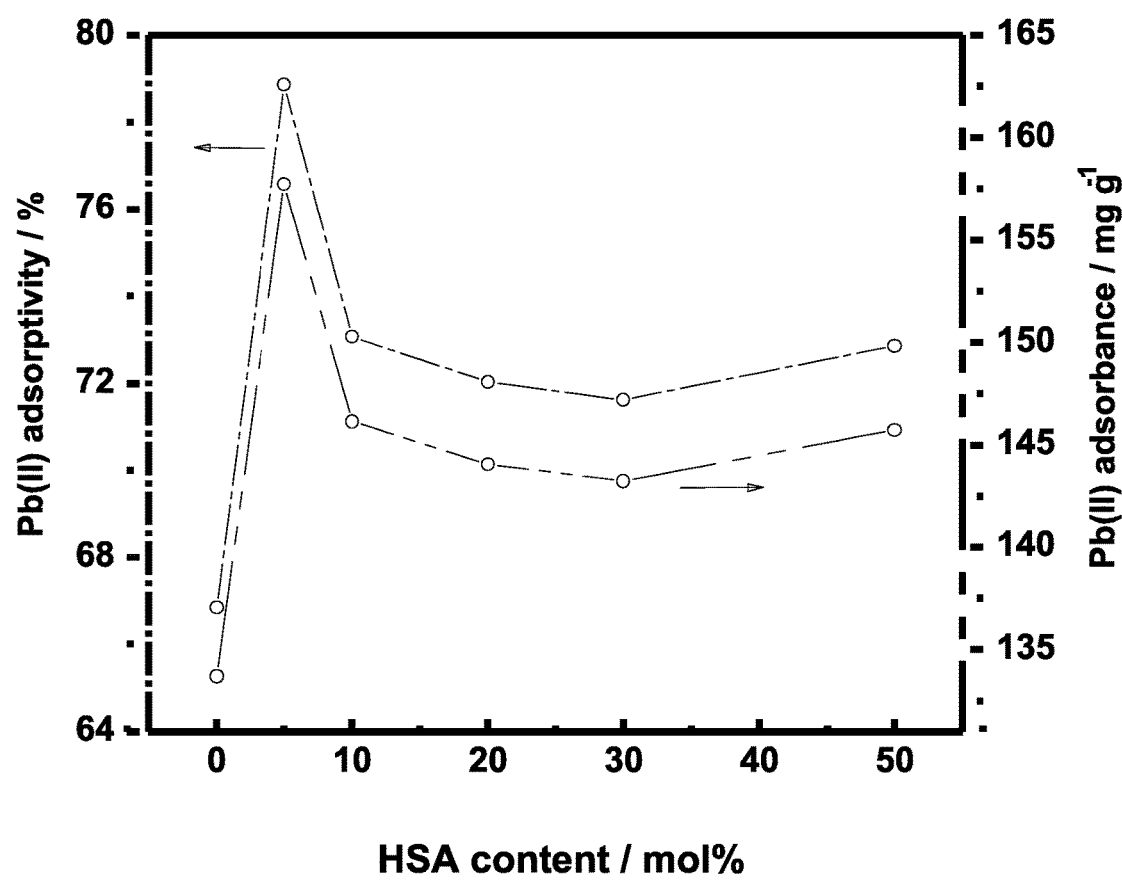
FIG. 7 is a plot showing adsorption of Pb(II) at an initial Pb(II) concentration of 0.965 mM onto mPD/HSA copolymer particles with a sorbent dose of 10 mg at 30° C. for 0.5 hour.

Without being bound by any specific theory, it is believed that one of the interactions between the poly(mPD-co-HSA) particles and Pb(II) ions is complexation of Pb(II) ions onto the ligating functional groups like —NH—, —N=, —OH, —SO$_3$H, and —NH$_2$ on the copolymer. FIG. 7 shows the complexation quantitatively by adsorption capacity and adsorptivity of Pb(II) onto the microparticles. The adsorption capability was found to be heavily dependent on the polymer composition. As shown in FIG. 7, as the HSA content increases from 0 to 50 mol %, the adsorbance and adsorptivity both significantly rose first and then decreased, demonstrating the maximal adsorbance and adsorptivity of 157.74 mg g$^{-1}$ and 78.87%, respectively, at the HSA content of 5 mol %. Compared to the mPD homopolymer particles, the mPD/HSA (95/5) copolymer particles have an adsorptivity enhancement by 12.02%, which is believed to attribute by the introduction of an optimal amount of ligating active sulfonic and hydroxyl groups and the best dispersion of the particles in Pb(II) aqueous solution as shown in FIG. 5. Thus, the interaction between the mPD/HSA (95/5) copolymer and Pb(II) ions is considered to be the strongest.

This Examples shows that Poly(mPD-co-HSA) copolymer particles are suitable to use as lead ionophores for Pb(II) ion-selective electrode (ISE).

Example 5

Synthesis of Polyaniline Nanosticks

Figure 8:
FIG. 8 is a scanning electron microscopy (SEM) image of virgin $HNO_3$-doped PAN nanosticks synthesized in 2.0 M $HNO_3$ with a fixed $(NH_4)_2S_2O_8$/monomer molar ratio of 0.6/1 at 0° C. for 6 hours.

In this example, polyaniline (PAN) nanosticks with higher electrical conductivity were synthesized by chemical oxidative polymerization of aniline. A procedure for the preparation of nanostructured PAN in 2M HNO$_3$ as acidic polymerization medium includes adding aqueous HNO$_3$ solution (2.M, 80 mL) with aniline (0.91 mL, 10 mmol) to a 250 mL glass flask in water bath at 0° C. and vigorously stirring the mixture for one hour. Ammonium persulfate (1.368 g, 6 mmol) was dissolved separately in HNO$_3$ (2 M, 20 mL) to prepare an oxidant solution that was kept in the same water bath. The oxidant solution was added dropwise to the monomer solution at a rate of one drop (60 μL) every 3 seconds at 0° C. over about 30 minutes. The reaction mixture was then continuously stirred for 6 hours in a water bath at 0° C. After the reaction, the virgin HNO$_3$-doped PAN salts formed were isolated from the reaction mixture by centrifugation and washed with an excess of distilled water to remove residual oxidant and water-soluble oligomers. Ultrasonic dispersion, washing, and centrifugation were repeated three or four times until no SO$_4^{2-}$ was detected by 1 M BaCl$_2$ solution. The purified dark green precipitate was left to dry under atmosphere at ambient temperature for one week. The yield of virgin HNO$_3$-doped PAN is 47.0%. The bulk electrical conductivity of the polymer particle sheet at 15 MPa is 50 S/cm by FZ-2010 semiconductor powder resistivity meter. Nominal structure and morphology of the PAN particle are shown in Scheme 2 and FIG. 8, respectively.

Scheme 2

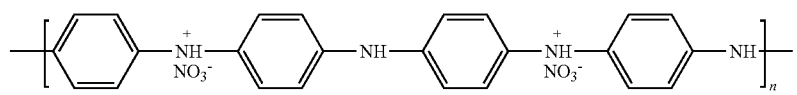

Example 6

Selection of Polymer Matrix Materials for Making Ion Selective Electrodes (ISE)

Physicochemical and mechanical properties of a number of polymer materials were tested in this example. Mechanical properties of the polymer membranes were measured by the universal material testing system (Model CMT5105), with a 100 N load cell. The membranes were cut into a rectangular tape and fixed on a metal frame and tested at room temperature with a gauge length of 30 mm and speed of 50 or 100 mm/min.

Table 1 shows some physicochemical parameters of five ethylene-vinyl acetate copolymer (EVA) elastomers with different vinyl acetate content, and mechanical behaviors of the corresponding vulcanized EVA. As shown in Table 1, EVA elastomer with 40% vinyl acetate has the highest resilient ratio among all EVA elastomers tested.

TABLE 1

Relationship between content of vinyl acetate and physicochemical parameters of EVA elastomer

| VAc content (%) | Tg, (° C.) | Vulcanized EVA rubber | | | |
|---|---|---|---|---|---|
| | | Crystallinity (%) | Tensile strength (MPa) | Elongation at breake (%) | Resilient rate (%) |
| 40 | −31 | 18.5 | 16.6 | 180 | 42 |
| 50 | −29 | 8.7 | 20.4 | 210 | 36 |
| 60 | −27 | Amorphous | 19.4 | 170 | 29 |
| 70 | −14 | Amorphous | 19.5 | 190 | 14 |
| 80 | −1 | Amorphous | 18.2 | 210 | 35 |

Table 2 shows the mechanical properties of a number of plasticizer-free matrix film of vinyl resin, LC-40, EVA elastomer. VAGD, VAGF and VAGH are inherently self-plasticizing vinyl resin. Among which, VAGD is a partially hydrolyzed vinyl resin and bears a certain amount of vinyl acetate and vinyl alcohol segments in the backbone that would weaken interactions between vinyl chloride macromolecular chains and thus properly soften the polymer materials.

Figure 9:
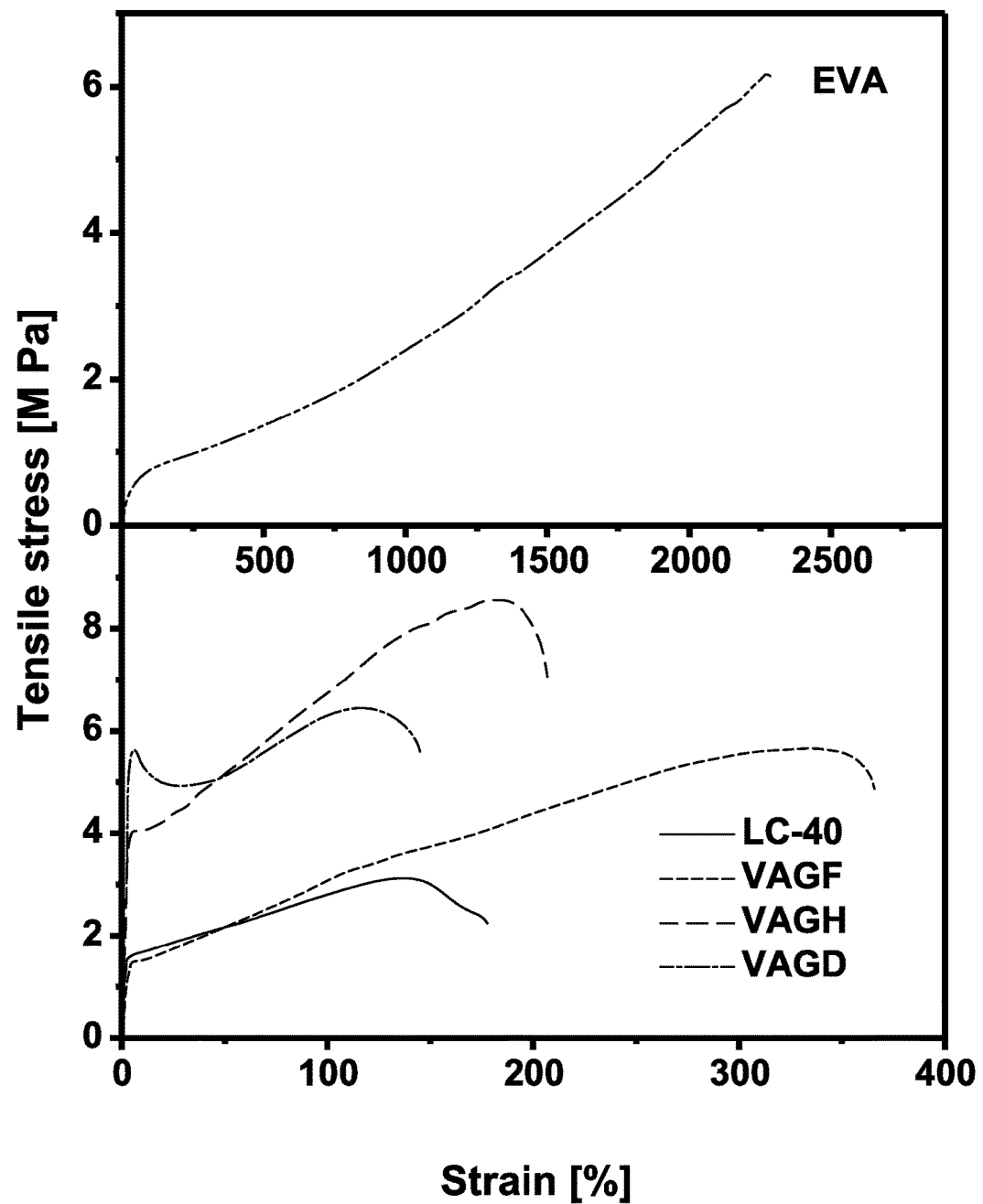
FIG. 9 is a plot showing strain-stress curves of plasticizer-free matrix films.

Table 1 shows that 40 wt % content of vinyl acetate segment disarranges well-defined structures of polyethylene chain and greatly decreased the crystallization degree of polyethylene, which makes EVA matrix material to exhibit high flexibility and high toughness. FIG. 9 and Table 2 show that the elongation at break of EVA film is up to 2284.8% and its breaking energy reaches 68.17 $J \cdot m^{-3}$. Summarily, tensile strength of EVA is comparable to those of vinyl chloride-vinyl acetate resins, while flexibility of EVA is much better than the latter.

This example shows that EVA elastomer is suitable for using as polymer matrix in ISE sensing membrane materials.

Example 7

Preparation of Pb(II) Sensing Membranes

In this example, EVA elastomer membranes and plasticized poly(vinyl chloride)(PVC) membranes containing poly(mPD-co-HSA) particles were prepared using the procedures described as follows. The resulting EVA-poly(mPD-co-HSA) membranes and PVC-poly(mPD-co-HSA) membranes were evaluated for use as Pb(II) sensing membranes.

The general procedure to prepare the plasticizer-free EVA-poly(mPD-co-HSA) membrane includes thoroughly mixing 300 mg of EVA, 10 mg of poly(mPD-co-HSA) particles and 15 mg of NaTPB in 5 mL of tetrahydrofuran (THF). The mixture was stirred at 25° C. to form a viscous solution while ultrasonic treatment was also performed to promote the dissolution or dispersion of the ionophore (i.e., poly(mPD-co-HSA) particles) for 2 hours and then casted into a 28 mm diameter glass ring that was affixed onto a glass plate. After the solvent was allowed to evaporate at

TABLE 2

Mechanical properties of plasticizer-free matrix film of vinyl resin

| Film[a] | Chain composition[b] (wt %) | Tg (° C.) | Thickness (μm) | Modulus of elasticity (MPa) | Tensile strength (MPa) | Elongation at break (%) | Breaking energy ($J \cdot m^{-3}$) |
|---|---|---|---|---|---|---|---|
| VAGD | VC/VAc/VA 90/4/6 | 77 | 308 | 163.5 | 6.45 | 144.6 | 8.13 |
| VAGH | VC/VAc/VA 90/4/6 | 79 | 275 | 163.2 | 8.55 | 206.7 | 13.61 |
| VAGF | VC/VAc/HA 81/4/15 | 70 | 280 | 59.9 | 5.66 | 365.8 | 14.60 |
| LC-40 | VC/VAc 60/40 | 60 | 317 | 87.4 | 3.14 | 177.7 | 4.39 |
| EVA Elastomer | E/VAc 60/40 | −31 | 492 | 2.6 | 6.16 | 2284.8 | 68.17 |

[a]Stretching rate was adopted 50 mm/min. But for EVA elastomer the stretching rate was elevated to 100 mm/min because it was not broken under stretching rate of 50 mm/min in given testing meter.
[b]E: Ethylene; VAc: Vinyl acetate; VC: Vinyl chloride; VA: Vinyl alcohol; HA: Hydroxyalkyl acetate As shown in Table 2 and FIG. 9, VAGD, VAGF and VAGH are harder materials with elastic modulus between 59.9 MPa and 163.5 MPa as compared to EVA elastomer. The decrease of glass temperatures of these vinyl resins in large amplitude is no higher than 15° C. compared with those of pure PVC (85° C.), and their breaking energies are about 10 $J \cdot m^{-3}$. Further improvement for toughness of the vinyl resin is limited when the content of vinyl acetate is below 20 wt %. For no hydrolyzed vinyl chloride-acetate copolymers, even if the vinyl acetate content is as high as 40 wt % the vinyl chloride chains are difficult to soften. For example, the Tg and breaking energy data shown in Table 2 and FIG. 9 indicate that LC-40 is not suitable for making matrix materials in ion selective electrodes (ISE).

room temperature for 24 hours, the resulting membranes were peeled off from the glass. Membrane discs of 14-mm diameter were cut out and glued onto a 10-mm inner diameter plastic tube. $10^{-4}$ M $Pb(NO_3)_2$ solution was used as an inner reference substance and Ag/AgCl electrode was employed as an inner reference electrode. The electrodes were conditioned in $10^{-4}$ M $Pb(NO_3)_2$ solution for 72 hours.

The general procedure to prepare PVC-poly(mPD-co-HSA) sensing membranes including thoroughly mixing 183 mg of plasticizer di-n-octyl phthalate (DOP), 99 mg of high molecular-mass PVC, 3 mg of ionophore (i.e., poly(mPD-co-HSA)), and 15 mg of oleic acid (OA) or 3 mg NaTPB as ion-exchanger in 5 mL of THF. The mixture was stirred at 25° C. to form a viscous solution while ultrasonic treatment was also performed to promote the dissolution or dispersion of the ionophore for 2 hours and then casted into a 28 mm diameter glass ring that was affixed onto a glass plate. After the solvent was allowed to evaporate at room temperature for 24 hours, the resulting membrane was peeled off from the glass and the membrane disc of 14-mm diameter was cut out and glued onto a 10-mm inner diameter plastic tube. $10^{-4}$ M $Pb(NO_3)_2$ solution was used as an inner reference substance and Ag/AgCl electrode was employed as an inner reference electrode. The electrode was conditioned in $10^{-4}$ M $Pb(NO_3)_2$ solution overnight.

Example 8

Preparation of Pb(II) Sensing Membranes with PAN Nanosticks

EVA-poly(mPD-co-HSA) membranes containing PAN nanosticks were prepared using the procedure described as follows. The resulting EVA-poly(mPD-co-HSA)-PAN membranes can be used as Pb(II) sensing membranes.

Poly(mPD-co-HSA) copolymer particles were prepared using the general procedures described in Example 1. Polyaniline (PAN) nanosticks were prepared using the procedures described in Example 5.

Example 9

Potentiometric Responses of Sensing Membranes Based on EVA Elastomer and PVC

Figure 10:
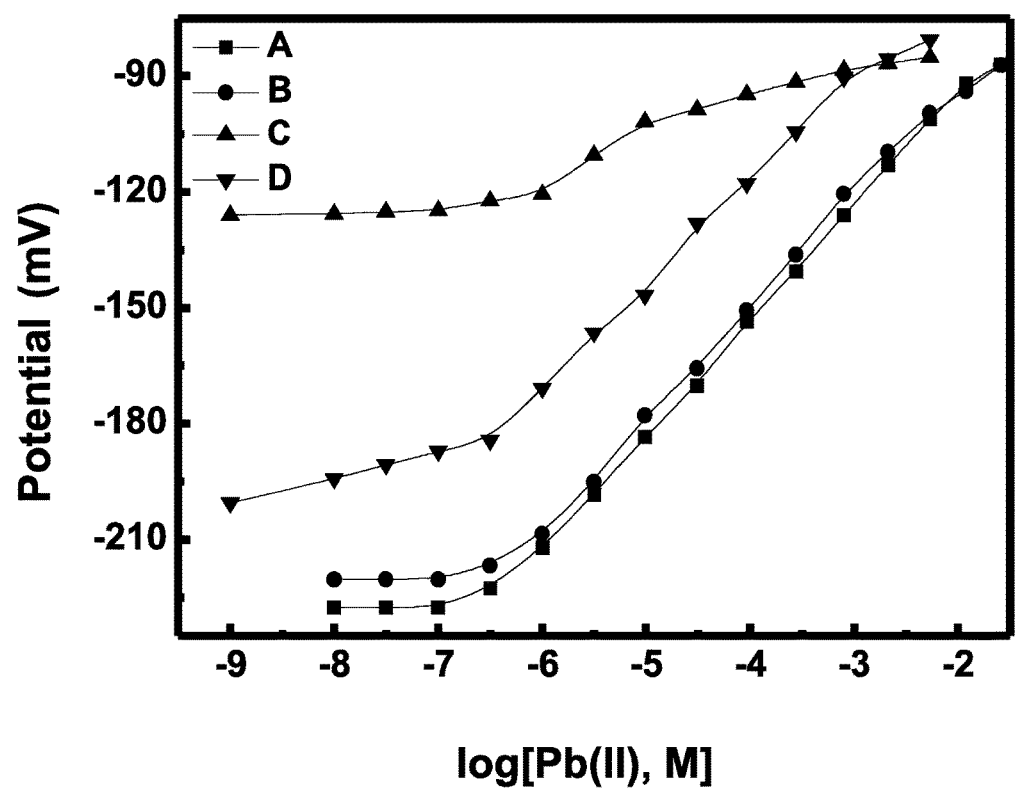
FIG. 10 is a plot showing potentiometric response curves of EVA elastomer membranes and PVC membranes with different ion-exchangers.

Various EVA-poly(mPD-co-HSA) sensing membranes and PVC-poly(mPD-co-HSA) sensing membranes were prepared according to the general procedure described in Example 7, except that various additives were introduced into the EVA and PVC sensing membranes, including oleic acid (OA) as ion exchanger and plasticizer. Potentiometric performance of the sensing membranes was studied by means of electrochemical impedance spectroscopy (EIS) between two copper sheets within the frequency range from $10^5$ to $10^{-2}$ Hz using 5 mV amplitude at the open circuit potential using CH-Instruments model 660D (Shanghai, China). The results are shown in FIG. 10 and Table 3. In FIG. 10, "A" represents the potentiometric response curve for a PVC membrane having a weight ratio of mPD/HSA:PVC:DOP:OA=1.0:33.0:61.0:5.0; "B" represents the potentiometric response curve for a PVC membrane having a weight ratio of mPD/HSA:PVC:DOP:NaTPB=1.0:33.0:65.0:1.0; "C" represents the potentiometric response curve for an EVA membrane having a weight ratio of mPD/HSA:EVA:OA=1.0:30:3.0; and "D" represents the potentiometric response curve for an EVA membrane having a weight ratio of mPD/HSA:EVA:NaTPB=1.0:30:1.5.

TABLE 3

Potentiometric responses Performances of EVA elastomer membrane and plasticized PVC with different ion-exchangers

| Matrix | Membrane composition (weight ratio) | Membrane thinkness (μm) | Potential fluctuation (mV) | Fitting range (M) |
|---|---|---|---|---|
| EVA elastomer | mPD/HSA:EVA:OA (1.0:30:3.0) | 117 | ±3 | $10^{-6.0}$-$10^{-5.0}$ |
| | mPD/HSA:EVA:NaTPB (1.0:30:1.5) | 120 | ±3 | $10^{-6.5}$-$10^{-3.1}$ |
| plasticized PVC | mPD/HSA:PVC:DOP:OA (1.0:33.0:61.0:5.0) | 150 | ±1 | $10^{-6.5}$~$10^{-1.9}$ |
| | mPD/HSA:PVC:DOP:NaTPB (1.0:33.0:65.0:1.0) | 150 | ±1 | $10^{-6.0}$~$10^{-2.3}$ |

| Matrix | R | Slope (mV/decade) | Detection limit (M) |
|---|---|---|---|
| EVA elastomer | 0.9992 | 18.9 | $10^{-6.30}$ ($5.01 \times 10^{-7}$) |
| | 0.9990 | 27.5 | $10^{-7.07}$ ($8.51 \times 10^{-8}$) |
| plasticized PVC | 0.9994 | 29.3 | $10^{-6.55}$ ($2.82 \times 10^{-7}$) |
| | 0.9995 | 29.7 | $10^{-6.38}$ ($4.17 \times 10^{-7}$) |

A general procedure for preparing a plasticizer-free EVA-poly(mPD-co-HSA)-PAN membrane include mixing 300 mg of EVA, 15 mg of poly(mPD-co-HSA) copolymer particles, 15 mg of sodium tetraphenylborate (NaTPB), and 1.6 mg of PAN in 5 mL of tetrahydrofuran (THF). The mixture was stirred at 25° C. to a viscous solution while ultrasonic treatment was also performed to promote the dissolution or dispersion of the ionophore for 2 hours and then casted onto a glass plate. After the solvent was evaporated at room temperature for 24 hours, the resulting membranes were peeled off from the glass.

As shown in FIG. 10, the slope of the sensing membrane with a composition mPD/HSA:EVA:NaTPB of 1.0:30.0:1.5 is 27.5 mV/decade, which is close to the theoretical Nernst slope of 15° C. (28.5 mV/decade). Moreover, the lower detection limit of the sensing membrane is $10^{-7.07}$ M, reduced by 0.69 orders of magnitude compared with corresponding plasticized PVC membrane matrix ($10^{-7.07}$M versus $10^{-6.38}$ M). Without being bound by any specific theory, the improvement of the lower detection limit is believed to be attributed to more dense membrane structure than that of plasticized PVC, which was helpful to suppress the ion flux and reduces interference to surface of EVA membrane. As also shown in FIG. 3 and Table 3, OA has ability to act as an effective ion exchanger with a slope of 29.3 mV/decade, whereas, OA was not suitable for plasticizer-free EVA sensing membrane because the observed slope of 18.9 mV/decade was far lower than the theoretical Nernst slope although OA can be used as ion-exchanger in plasticized PVC. This is probably because OA does not ionize to generate relatively high content OK in plasticizer-free EVA elastomer, which leads to failure of Donnan exclusion.

This example shows that EVA-poly(mPD-co-HSA) sensing membranes can be used in ISE with good sensitivity.

Example 10

Determination of Suitable Ion-Exchanger Contents in Pb(II) Sensing Membrane

Figure 11:
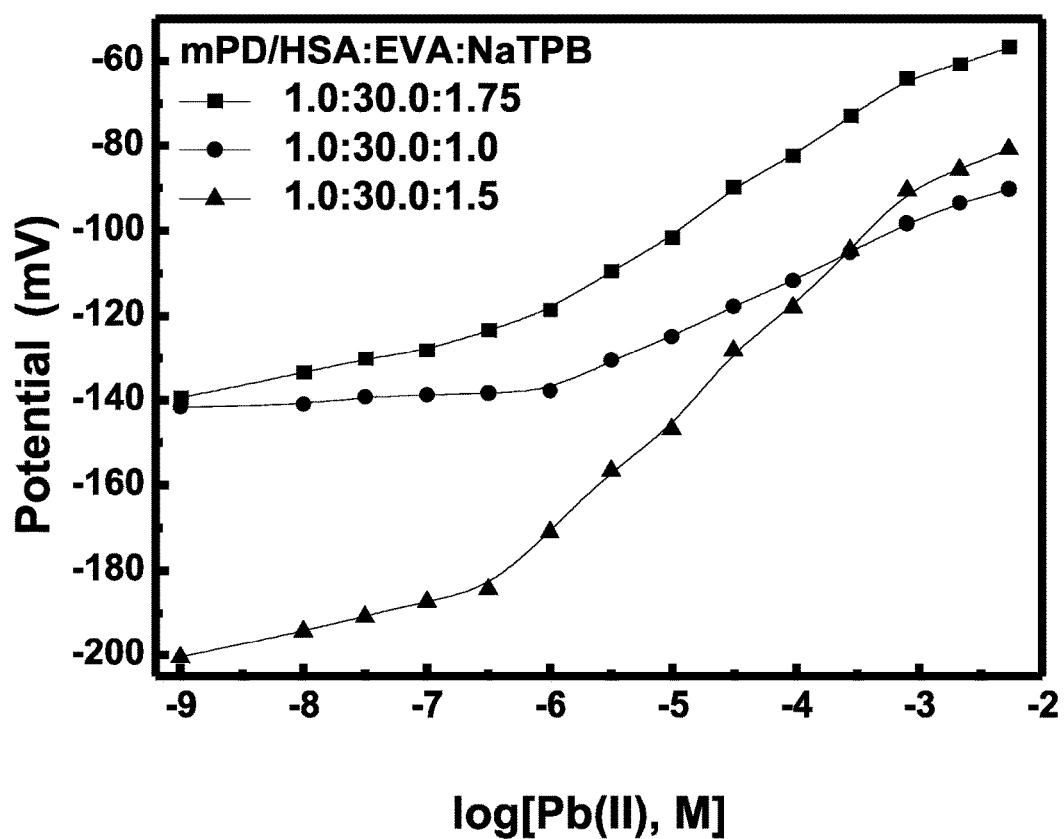
FIG. 11 is a plot showing potentiometric responses curve of EVA elastomer membrane with different content of ion-exchangers.

EVA-poly(mPD-co-HSA) membranes were prepared using the procedure described in Example 7 except that various amount of ion-exchanger NaTPB was used. The prepared EVA-poly(mPD-co-HSA) membranes was used as Pb(II) sensing membranes in the ISEs. Potentiometric performance of the sensing membranes was determined. The results are shown in FIG. 11 and Table 4.

This example shows that EVA:NaTPB with a weight ratio of 30:1.5 is suitable for use in a Pb(II) sensing membrane.

Example 11

Determination of Suitable Ionophore Contents in Pb(II) Sensing Membrane

Figure 12:
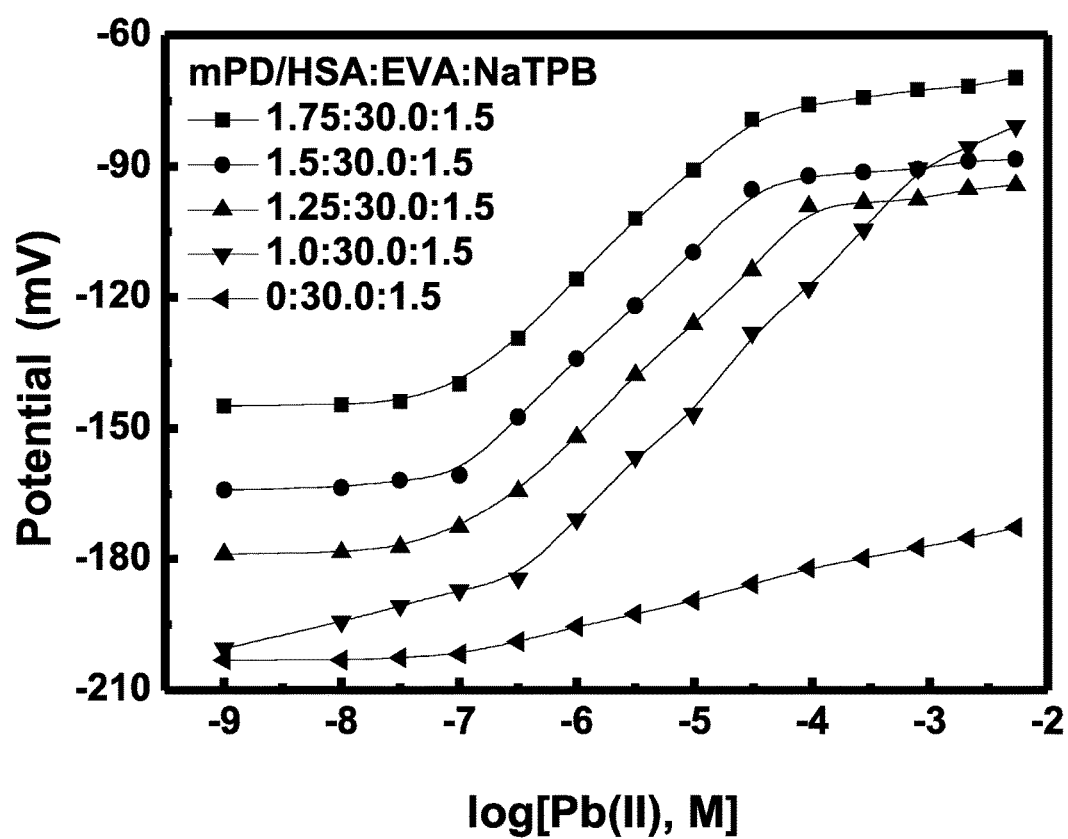
FIG. 12 is a plot showing potentiometric responses curve of EVA elastomer membrane with different content of ionophores.

EVA-poly(mPD-co-HSA) membranes were prepared using the procedure described in Example 7 except that various amount of ionophore poly(mPD-co-HSA) copolymer particles were used. The prepared EVA-poly(mPD-co-HSA) membranes was used as Pb(II) sensing membranes in the ISEs. Potentiometric performance of the sensing membranes was determined. The results are shown in FIG. 12 and Table 5.

TABLE 4

Performance of EVA-poly(mPD-co-HSA) sensing membrane with different content of ion-exchangers

| mPD/HSA: EVA:NaTPB (wt %) | NaTPB content (wt %) | Membrane thickness (μm) | Potential fluctuation (mV) | Fitting range (M) | R | Slope (mV/decade) | Detection limit (M) |
|---|---|---|---|---|---|---|---|
| 1.0:30:1.0 | 3.1 | 120 | ±4 | $10^{-6.0}$-$10^{-3.1}$ | 0.9992 | 18.8 | $10^{-7.09}$ ($8.13 \times 10^{-8}$) |
| 1.0:30:1.5 | 4.6 | 120 | ±3 | $10^{-6.5}$-$10^{-3.1}$ | 0.9990 | 27.5 | $10^{-7.07}$ ($8.51 \times 10^{-8}$) |
| 1.0:30:1.75 | 5.3 | 117 | ±2 | $10^{-6.0}$-$10^{-2.7}$ | 0.9993 | 13.4 | $10^{-6.28}$ ($5.25 \times 10^{-7}$) |

As shown in Table 4 and FIG. 11, slope of the sensing membrane with a composition of mPD/HSA:EVA:NaTPB=1.0:30:1.0 is 18.8 mV/decade. The sub-nernst function may be caused by lack of enough NaTPB, which would

TABLE 5

Performance of EVA-poly(mPD-co-HSA) sensing membrane with different content of ionophore

| mPD/HSA: EVA:NaTPB (wt %) | Membrane thickness (μm) | Ionophore content (wt %) | Potential fluctuation (mV) | Fitting range (M) | R | Slope (mV/decade) | Detection limit (M) |
|---|---|---|---|---|---|---|---|
| 0:30:1.5 | 120 | 0 | ±3 | $10^{-7.0}$-$10^{-2.3}$ | 0.9988 | 6.2 | $10^{-7.26}$ ($5.49 \times 10^{-8}$) |
| 1.0:30:1.5 | 120 | 3.1 | ±3 | $10^{-6.5}$-$10^{-3.1}$ | 0.9990 | 27.5 | $10^{-7.07}$ ($8.51 \times 10^{-8}$) |
| 1.25:30:1.5 | 120 | 3.8 | ±3 | $10^{-6.5}$-$10^{-4.0}$ | 0.9995 | 26.1 | $10^{-7.05}$ ($8.91 \times 10^{-8}$) |
| 1.5::30:1.5 | 109 | 4.5 | ±4 | $10^{-7.0}$-$10^{-4.5}$ | 0.9997 | 26.0 | $10^{-7.13}$ ($7.41 \times 10^{-8}$) |
| 1.75::30:1.5 | 120 | 5.3 | ±4 | $10^{-7.0}$-$10^{-4.5}$ | 0.9992 | 24.8 | $10^{-7.18}$ ($6.61 \times 10^{-8}$) | lead to failure of Donnan exclusion. When the amount of NaTPB was increased to 4.6 (wt) %, the slope of the EVA elastomer membrane with a composition of mPD/HSA:EVA:NaTPB=1.0:30:1.5 is 27.5 mV/decade (at 15° C.). The slope of the sensing membrane with 5.3 (wt) % NaTPB is 13.4 mV/decade.

As shown in FIG. 12 and Table 5, the slope of the sensing membrane without ionophore is only 6.2 mV/decade, and no Nestian response was observed. In order to examine the effect of the ionophore concentration in EVA-poly(mPD-co-HSA) sensing membrane, four kinds of EVA-poly(mPD-co-HSA) sensing membranes with different poly(mPD-co- HSA) particle content were examined. The membranes with mPD/HSA:EVA:NaTPB weight ratio of 1.0:30:1.5, or 1.25:30:1.5, or 1.5:30:1.5 (the ionophore content is between 3.1 wt %-4.5 wt % in these membranes) all showed acceptable response slope owing to complexation of the sufficient ionophore with Pb(II). However, when the ionophore content increased to 5.3 wt %, the slope of the sensing membrane decreased to 24.8 mV/decade. Such a sub-Nernst effect may be caused by the failure of Donnan exclusion because of the presence of too many poly(mPD-co-HSA) ionophores.

This example shows that EVA-poly(mPD-co-HSA) membranes with mPD/HSA:EVA:NaTPB weight ratio of 1.0:30:1.5, 1.25:30:1.5, or 1.5:30:1.5 are suitable for use as a Pb(II) sensing membrane.

Example 12

Determination of Suitable Electrical Conducting Additives in Pb(II) Sensing Membrane To build an anti-electrostatic sensing membrane, conducting additives were added into the EVA elastomer matrix to avoid any slight fracture or pinhole in the solid membrane. The amount of the conducting additives was less than 1 wt % of the total weight of the polymer matrix. Two electrical conducting additives, carbon nanotubes and PAN nanosticks were used. Purified multi-walled carbon nanotubes with length of 10~30 µm, diameter of 5~8 nm, special surface area of >500 m$^2$/g, electrical conductivity of >100 S/cm (obtained from Chengdu Organic Chemicals Co. Ltd., Chinese Academy of Sciences) were added to EVA elastomer matrix. The carbon nanotubes were found to aggregate and could not disperse uniformly in the EVA matrix due to the absent of functional groups on carbon nanotubes.

Polyaniline (PAN) nanosticks of 50 S/cm were prepared according to the general procedure described in Example 5. The prepared PAN nanosticks were introduced into the EVA elastomer matrix, and uniform dispersion of the composite system was observed. Formation of hydrogen bonds between the functional groups (such as —NH—) on polyaniline chain and the oxygen atoms in vinyl acetate units of EVA chain is illustrated in Scheme 3. Without being bound by any specific theory, it is believed that the hydrogen bonds formed between PAN and EVA chains facilitate the dispersion of PAN in EVA polymer matrix.

Scheme 3

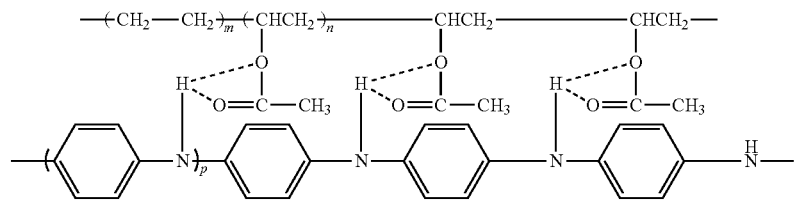

Figure 13:
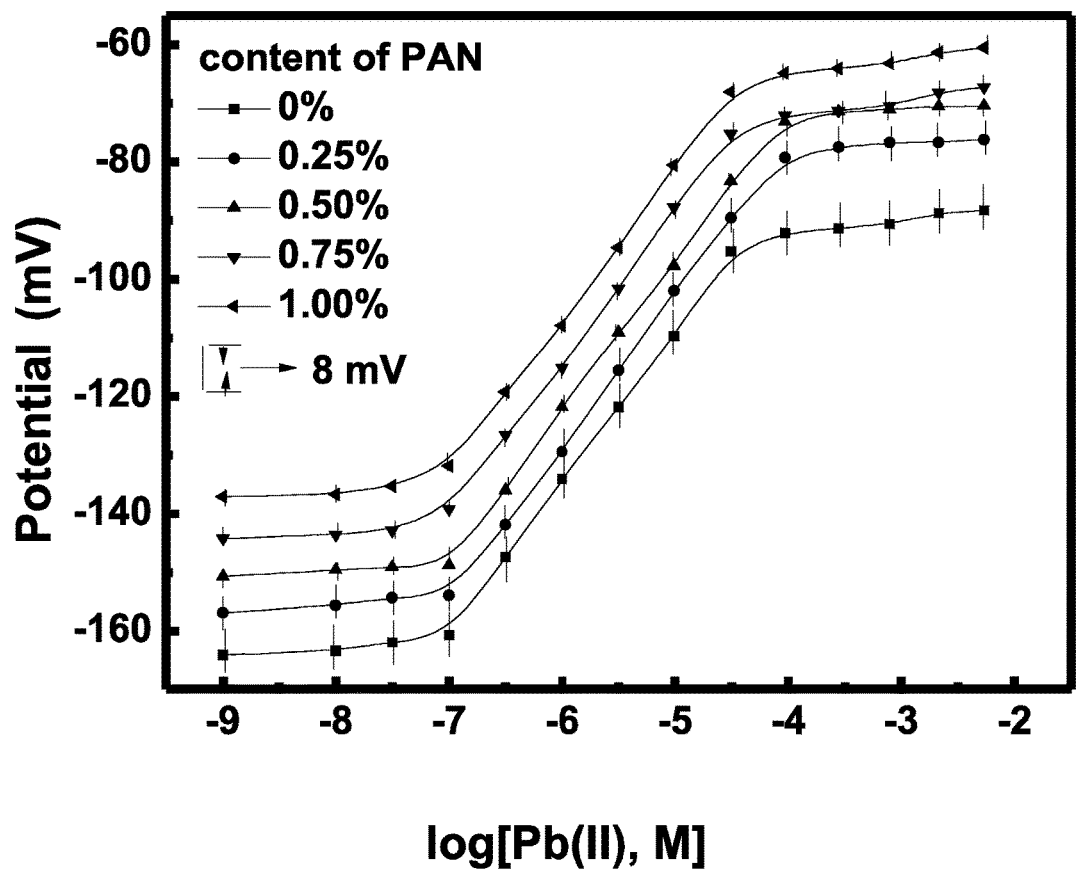
FIG. 13 is a plot showing potentiometric responses curve of EVA elastomer membrane with different content of PAN.

As shown in FIG. 13 and Table 6, EVA elastomer membranes loaded with PAN nanosticks show more stable potentials than the EVA elastomer membrane without any PAN nanosticks, and no observable loss in sensing performance.

TABLE 6

Performance of EVA elastomer membrane with different content of PAN

| mPD/HSA:EVA:NaTPB:PAN (weight ratio) | PAN content (wt %) | Membrane thickness (µm) | potential fluctuation (mV) | Fitting range (M) |
| --- | --- | --- | --- | --- |
| 1.5:30:1.5:0 | 0 | 109 | ±4 | $10^{-7.0}$-$10^{-4.5}$ |
| 1.5:30:1.5:0.081 | 0.25 | 120 | ±3 | $10^{-7.0}$-$10^{-4.5}$ |
| 1.5:30:1.5:0.1625 | 0.49 | 120 | ±1.5 | $10^{-7.0}$-$10^{-4.5}$ |
| 1.5:30:1.5:0.24 | 0.73 | 120 | ±1.5 | $10^{-7.0}$-$10^{-4.5}$ |
| 1.5:30:1.5:0.33 | 0.98 | 120 | ±1.5 | $10^{-7.0}$-$10^{-4.5}$ |

| mPD/HSA:EVA:NaTP:PAN (weight ratio) | R | Slope (mV/decade) | Detection limit (M) |
| --- | --- | --- | --- |
| 1.5:30:1.5:0 | 0.9997 | 26.0 | $10^{-7.13}$ (7.41 × $10^{-8}$) |
| 1.5:30:1.5:0.081 | 0.9997 | 26.1 | $10^{-71.0}$ (7.94 × $10^{-8}$) |
| 1.5:30:1.5:0.16 | 0.9997 | 26.1 | $10^{-7.08}$ (8.32 × $10^{-8}$) |
| 1.5:30:1.5:0.24 | 0.9995 | 25.8 | $10^{-7.18}$ (6.61 × $10^{-8}$) |
| 1.5:30:1.5:0.33 | 0.9995 | 25.7 | $10^{-7.21}$ (6.17 × $10^{-8}$) |

For example, for the EVA membrane loaded with 0.25 wt % of PAN nanosticks, potential fluctuation was decreased from ±4.0 mV to ±3.0 mV. With the amount of PAN nanosticks increased to 0.49 wt % inside the membrane, the potential fluctuation was greatly decreased to ±1.5 mV and the membrane also showed the same responses characteristics. The improved stabilities of potential readings are mainly attributed to the formation of continuous PAN conductive networks with abundant π electrons, which allow conducting particles in/or on membrane to flow more freely in the whole membrane bulk as well as along backbone of PAN. As a result, static electricity can be discharged and cannot be accumulated on membrane. On the other hand, no further improvement in stabilities of potential readings was observed when content of PAN nanosticks was further enhanced to respective 0.73 wt % and 0.98 wt %, and oppositely, lower response slopes were observed in these circumstances. This may be because the excessive PAN, being a foreign component, would cause a certain degree of damage to the membrane in form of craze and pinhole. Also abundant of imine and amine groups on PAN chains can provide too many complexation sites for lead ions. As a result, too many nitrate ions are accompanied at two sides of the sensing membrane, which directly lead to invalid of Donnan exclusion.

This example shows that EVA elastomer membranes with a content of PAN nanosticks 0.49 wt % are suitable for use as a Pb(II) sensing membrane.

Example 13

Assembly of a Potentiometric Pb(II) Sensor

An EVA-poly(mPD-co-HSA)-PAN sensing membrane was prepared using the procedure described in Example 8. In this example, a potentiometric Pb(II) sensor was assembled using the procedure described as follows.

An EVA-poly(mPD-co-HSA)-PAN membrane was cut into a circular membrane of 14 mm diameter and glued onto one end of a 10-mm inner diameter plastic tube. $10^{-4}$ M $Pb(NO_3)_2$ solution was used as an inner reference substance and filled into the plastic tube. Ag/AgCl electrode was employed as an inner reference electrode. The as-prepared electrodes were conditioned in $10^{-4}$ M $Pb(NO_3)_2$ solution 72 hours and then washed by water until a stable potential was reached before using.

All response potentials were examined by using the following assembly setup: Ag|AgCl|KCl (saturated solution)||Pb(NO)$_3$ (1.00×$10^{-4}$M)|EVA-poly(mPD-co-HSA)-PAN sensing membrane |Test solution||KNO$_3$ (1.00M)||KCl (saturated solution)|Hg$_2$Cl$_2$|Hg Saturated calomel electrode (SCE) was applied as an outer reference electrode and the cell potential was measured by varying the concentration of test solutions in a range between 1.00×$10^{-9}$ and 1.00×$10^{-2}$ M. Potentials were measured with PXSJ-216 potentiometer (Shanghai Lei ci Instruments Factory, China) with a sensitivity of 0.1 mV and an input resistance of great than 1×$10^{12}$Ω.

Example 14

Response Time of EVA-Poly(mPD-Co-HSA) Sensing Membranes

A potentiometric Pb(II) sensor based on the EVA-poly (mPD-co-HSA)-PAN sensing membrane was assembled using the procedure described in Example 13 with a weight ratio of mPD/HSA:EVA:NaTPB:PAN of 1.5:30:1.5:0.16.

Figure 14:
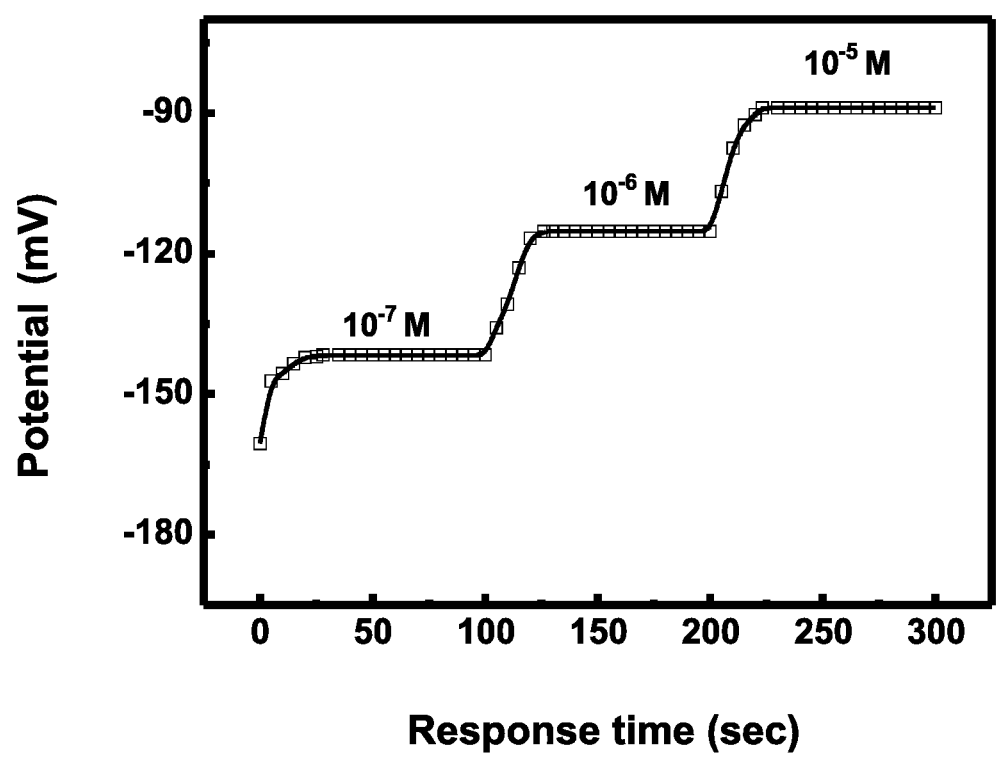
FIG. 14 is a plot showing response time profile of the EVA elastomer membrane with mPD/HSA:EVA:NaTPB:PAN weight ratio of 1.5:30:1.5:0.16.

FIG. 14 shows measured potentials of the EVA-poly (mPD-co-HSA)-PAN sensing membrane corresponding to one decade additions of $Pb(NO_3)_2$ solution from background till $10^{-5}$ M. The transient response observed for the one-decade step concentration changes had the typical exponential profile in all the cases. The response time ($t_{90}$%) for the membrane was less than 30 seconds.

This example shows that EVA-poly(mPD-co-HSA)-PAN sensing membranes can respond to Pb(II) quickly.

Example 15 pH Windows of EVA-Poly(mPD-Co-HSA) Sensing Membranes

A potentiometric Pb(II) sensor based on the EVA-poly (mPD-co-HSA)-PAN sensing membrane was assembled using the procedure described in Example 13 with a weight ratio of mPD/HSA:EVA:NaTPB:PAN of 1.5:30:1.5:0.16.

Figure 15:
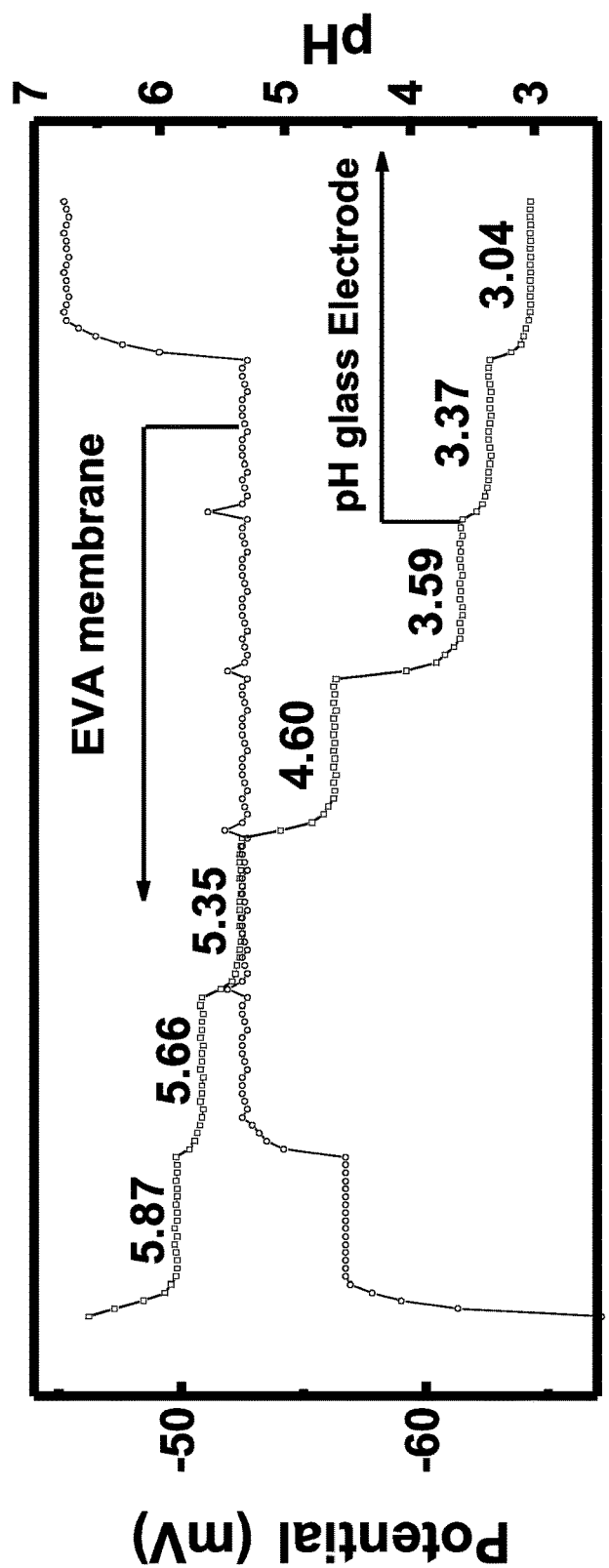
FIG. 15 is a plot showing the effect of pH on the EVA elastomer membrane with mPD/HSA: EVA: NaTPB: PAN weight ratio of 1.5:30:1.5:0.16.

The effect of pH on the EVA elastomer membrane was studied by adjusting pH of the sample over the range of 3.04-5.91 by adding a dilute $HNO_3$ or NaOH to a 1.0×$10^5$ M $Pb^{2+}$ solution. As shown in FIG. 15, within the range pH 3.37 to pH 5.68, the potential values of the membrane did not vary by more than 1 mV. Without being bound to any particular theory, it is believe that the change in the electrode response at higher pH values (pH>5.68) may be due to the hydrolysis of the $Pb^{2+}$ ions or formation of lead hydroxy complexes ($Pb(OH)^+$). By contrast, at lower pH (pH<3.37), variation of potential could be related to the responds to the hydrogen ions, which resulted in a loss of its ability to form complexes with the $Pb^{2+}$ ions.

Example 16

Specificity of EVA-Poly(mPD-Co-HSA) Sensing Membranes

A potentiometric Pb(II) sensor based on the electrostatic EVA copolymer elastomer membrane was assembled using the procedure described in Example 13 with a weight ratio of mPD/HSA:EVA:NaTPB:PAN of 1.5:30:1.5:0.16.

Potentiometric selectivity coefficients reflect the relative response of the membrane sensor for the primary ion over other ions present in solution. The selectivity coefficients of the EVA copolymer elastomer membrane to seventeen common cations were investigated by the fixed interference method. The potential was measured in solutions containing a fixed amount of interfering ion (1.0×$10^4$ M) and varying amounts of the primary ions ($Pb^{2+}$), and the potentiometric selectivity coefficients ($K_{Pb,M}^{pot}$) were evaluated according to the following expression:

$$K_{Pb,M}^{pot} = \frac{a_{Pb}}{a_M^{2/z_M}} \quad (2)$$

where $a_{Pb}$ is the activity of Pb(II) ion, $a_M$ is the activity of the interfering ion, and $z_M$ is the valence number of the interfering ion. According to this equation, the selectivity coefficients ($K_{Pb,M}^{pot}$) of the EVA copolymer elastomer membrane were evaluated, and a summary of the results are shown in Table 7.

TABLE 7

Selectivity coefficients of the EVA elastomer membrane with mPD/HSA:EVA:NaTPB:PAN weight ratio of 1.5:30:1.5:0.1625

| Interfering ion | Detection limit $a'_{Pb}$ (M) | Selectivity coefficient $K_{Pb,B}^{pot}$ (EVA) | Selectivity coefficient $K_{Pb,B}^{pot}$ (plasticized PVC) |
|---|---|---|---|
| $Ag^+$ | $10^{-7.12}$ | $10^{0.88}$ | $10^{0.5}$ |
| $Na^+$ | $10^{-7.12}$ | $10^{0.88}$ | $10^{-0.1}$ |
| $NH_4^+$ | $10^{-7.20}$ | $10^{0.80}$ | $10^{0.6}$ |
| $K^+$ | $10^{-7.18}$ | $10^{0.82}$ | $10^{-0.3}$ |
| $Ca^{2+}$ | $10^{-6.87}$ | $10^{-2.87}$ | $10^{-3.1}$ |
| $Mg^{2+}$ | $10^{-6.97}$ | $10^{-2.97}$ | $10^{-3.1}$ |
| $Ba^{2+}$ | $10^{-6.72}$ | $10^{-2.72}$ | $10^{-2.4}$ |
| $Cu^{2+}$ | $10^{-6.86}$ | $10^{-2.86}$ | $10^{-2.4}$ |
| $Zn^{2+}$ | $10^{-6.63}$ | $10^{-2.63}$ | $10^{-2.6}$ |
| $Mn^{2+}$ | $10^{-6.92}$ | $10^{-2.92}$ | $10^{-2.8}$ |
| $Co^{2+}$ | $10^{-6.64}$ | $10^{-2.64}$ | $10^{-2.3}$ |
| $Ni^{2+}$ | $10^{-6.77}$ | $10^{-2.77}$ | $10^{-3.2}$ |
| $Cd^{2+}$ | $10^{-6.72}$ | $10^{-2.72}$ | $10^{-2.3}$ |
| $Hg^{2+}$ | $10^{-5.89}$ | $10^{-1.89}$ | $10^{-0.5}$ |
| $Al^{3+}$ | $10^{-6.95}$ | $10^{-4.28}$ | $10^{-3.7}$ |
| $Cr^{3+}$ | $10^{-7.11}$ | $10^{-4.44}$ | $10^{-3.2}$ |
| $Fe^{3+}$ | $10^{-7.07}$ | $10^{-4.40}$ | $10^{-3.7}$ |

As shown in Table 7, except for Hg(II) ion, the selectivity coefficient for all divalent metal ions examined generally was about $10^{-3}$ or smaller, indicating that these metal ions would not significantly disturb the testing of Pb(II). For monovalent interfering ions and Hg(II) ion, the selectivity coefficients are higher than $10^{-2}$, which indicates some reversible interfering effect in the EVA sensing membrane. Without being bound to any specific theory, it is believed that the superior selectivity of the EVA elastomer membrane may be a result from lower diffusion coefficient of the solid EVA matrix.

This example shows that the EVA elastomer membrane are highly selective toward Pb(II).

Example 17

Lifetime Evaluation of the EVA-Poly(mPD-Co-HSA) Membranes

Potentiometric Pb(II) sensors based on EVA-poly(mPD-co-HSA)-PAN sensing membranes were assembled using the procedure described in Example 13. Operating lifetime of the sensing membrane (with a thickness of ca. 150 μm) was evaluated with inner solution of $10^{-4}$ M $Pb(NO_3)_2$ by recording its potential and plotting its calibration curve each week. Table 8 shows that there was no significant change in the slope and detection limit on the following week. The EVA sensing membrane was tested over a period of 16 weeks to investigate its lifetime, and no serious defect was observed (that is, there was little change in their detection limit and slope).

TABLE 8

Response change of EVA elastomer membrane with usage time

| Time (Week) | Linear range (M) | Fitting equation | R | Slope (mV/decade) | Detection limit (M) |
|---|---|---|---|---|---|
| 0 | $10^{-7.0}$-$10^{-4.5}$ | E = 34.2 + 26.1 log a | 0.9997 | 26.13 | $10^{-7.08}$ (8.32 × $10^{-8}$) |
| 1 | $10^{-7.0}$-$10^{-4.5}$ | E = 34.9 + 26.1 log a | 0.9996 | 26.10 | $10^{-7.08}$ (8.32 × $10^{-8}$) |
| 2 | $10^{-7.0}$-$10^{-4.5}$ | E = 35.9 + 26.1 log a | 0.9995 | 26.11 | $10^{-7.08}$ (8.32 × $10^{-8}$) |
| 3 | $10^{-7.0}$-$10^{-4.5}$ | E = 36.5 + 26.0 log a | 0.9995 | 26.04 | $10^{-7.06}$ (8.71 × $10^{-8}$) |
| 4 | $10^{-7.0}$-$10^{-4.5}$ | E = 37.3 + 26.0 log a | 0.9995 | 26.03 | $10^{-7.06}$ (8.71 × $10^{-8}$) |
| 6 | $10^{-7.0}$-$10^{-4.5}$ | E = 38.7 + 26.0 log a | 0.9996 | 26.03 | $10^{-7.05}$ (8.91 × $10^{-8}$) |
| 8 | $10^{-6.5}$-$10^{-4.5}$ | E = 39.8 + 26.0 log a | 0.9994 | 25.96 | $10^{-6.97}$ (1.07 × $10^{-7}$) |
| 10 | $10^{-6.5}$-$10^{-4.5}$ | E = 40.3 + 26.0 log a | 0.9994 | 25.96 | $10^{-6.98}$ (1.05 × $10^{-7}$) |
| 12 | $10^{-6.5}$-$10^{-4.5}$ | E = 41.5 + 25.9 log a | 0.9994 | 25.94 | $10^{-6.97}$ (1.07 × $10^{-7}$) |
| 14 | $10^{-6.5}$-$10^{-4.5}$ | E = 41.9 + 25.9 log a | 0.9995 | 25.86 | $10^{-6.92}$ (1.20 × $10^{-7}$) |
| 16 | $10^{-6.5}$-$10^{-4.5}$ | E = 41.9 + 25.6 log a | 0.9995 | 25.63 | $10^{-6.75}$ (1.78 × $10^{-7}$) |

This Example shows that the potentiometric Pb(II) sensor based on the electrostatic EVA copolymer elastomer has a long operating lifetime.

Example 18

Detection of Pb(II) in Real-World Samples

Potentiometric Pb(II) sensors based on EVA-poly(mPD-co-HSA) sensing membranes were assembled using the procedure described in Example 13.

Tap water from Tongji University was collected. Because the lead(II) concentration in the collected tap water was beyond linear range of the proposed Pb(II)-sensors, the lead(II) concentration in tap water was spiked. To avoid the interference from background ions in the real samples, Gran's plot was used to conduct the measurement. The recoveries and the relative standard deviation (RSD) were 98.9% and 3.1%, respectively. Furthermore, the results of the spiked tap water were confirmed by AAS method, giving a small relative error of 4.38%.

This example demonstrates that the potentiometric Pb(II) sensor based on the electrostatic EVA copolymer elastomer can be used to reliably detect Pb(II) in real-world examples.

Example 19

Comparison of Pb(II)-ISEs

Potentiometric Pb(II) sensors based on the EVA-poly(mPD-co-HSA) sensing membranes was assembled using the procedure described in Example 13. The assembled Pb(II) sensor was compared with a few known Pb(II) ISE with plasticized PVC as the polymer matrix, and the results are shown in Table 9.

TABLE 9

Comparison of Pb(II)-ISE in plasticized PVC based on Poly(mPD-co-HSA) ionophore and other ionophores described in the literature

| Ionophore | Fitting range (M) | Slope (mV/decade) | Detection limit (M) |
|---|---|---|---|
| Poly(mPD-co-HSA) | $3.2 \times 10^{-7}$ to $1.3 \times 10^{-2}$ | 29.3 | $2.8 \times 10^{-7}$ |
| PmPD | $3.2 \times 10^{-6}$ to $3.2 \times 10^{-2}$ | 29.8 | $6.3 \times 10^{-7}$ |
| 1,3-bis(N'-Benzoylthioureido)-benzene | $4.0 \times 10^{-6}$ to $1.0 \times 10^{-2}$ | 31.5 | $1.6 \times 10^{-6}$ |
| phenyl hydrazone derivative | $7.7 \times 10^{-7}$ to $1.0 \times 10^{-1}$ | 29.5 | $3.2 \times 10^{-7}$ |

| Ionophore | Response time (s) | pH range | Lifetime (month) |
|---|---|---|---|
| Poly(mPD-co-HSA) | 16 | 3.6-5.6 | 5 |
| PmPD | 14 | 3.0-5.0 | 5 |
| 1,3-bis(N'-Benzoylthioureido)benzene | 14 | 2.2-6.0 | >2 |
| phenyl hydrazone derivative | 6 | 3.7-6.3 | 2.5 |

TABLE 10

Comparison of the Pb(II)-ISE in EVA matrix with other Pb(II)-ISE with plasticizer-free membranes

| Ionophore | Matrix | Fitting range (M) | Slope (mV/decade) | Detection limit (M) |
|---|---|---|---|---|
| Poly(mPD-co-HSA) | EVA | $10^{-6.5}$-$10^{-3.1}$ | 27.48 | $8.51 \times 10^{-8}$ |
| tert-butylcalix[4]arene-tetrakis(N,N-dimethylthioacetamide) | nBA | $10^{-5}$-$10^{-1}$ | 26.6 | $10^{-5}$ |
| tert-butylcalix[4]arene-tetrakis(N,N-dimethylthioacetamide) | nBA + HEMA | $10^{-9}$-$10^{-2}$ | 26.2 | $10^{-9}$ |
| N,N'-diheptyl-N,N',6,6-tetramethyl-4,8-dioxaundecanediamide | IDA + AN/HDDA | $10^{-5}$-$10^{-2}$ | 28.0 | $10^{-6}$ | nBA: n-butyl acrylate,
HEMA: hydroxyethyl methacrylate,
IDA: isodecyl acrylate,
AN: acrylonitrile,
HDDA: 1,6-hexanedioldiacrylate,
MMA: methyl methacrylate,
DMA: n-decyl methacrylate.

This example demonstrates that the potentiometric Pb(II) sensor based on the EVA-poly(mPD-co-HSA) sensing membrane can be used to detect Pb(II).

In at least some of the previously described embodiments, one or more elements used in an embodiment can interchangeably be used in another embodiment unless such a replacement is not technically feasible. It will be appreciated by one of ordinary skill in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, one of ordinary skill in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, one of ordinary skill in the art will recognize that the disclosure is also thereby described in terms of any individual member or subgroup of members of the Markush group.

As will be understood by one of ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one of ordinary skill in the art all language such as "up to," "at least," "greater than," "less than," and the like include the number recited and refer to ranges which can be subsequently broken down into sub-ranges as discussed above. Finally, as will be understood by one of ordinary skill in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to one of ordinary skill in the art. The various aspects and embodiments disclosed herein are for purposes of illustration and are not intended to be limiting, with the true scope and spirit being indicated by the following claims.

One of ordinary skill in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

What is claimed is:

1. A copolymer comprising at least one optionally substituted 2-hydroxy-5-sulfonic aniline as a first constituent unit and at least one optionally substituted phenylenediamine as a second constituent unit, wherein the first constituent unit is present in the copolymer in an amount of about 5% to about 10% by mole and the second constituent unit is present in the copolymer in an amount of about 90% to about 95% by mole, and wherein particles of the copolymer have an average diameter of about 2000 nm.

2. The copolymer of claim 1, wherein the first constituent unit is represented by Formula I:

wherein $R^1$ is hydrogen or an electron-donating group, and $R^2$ is hydrogen or an electron-donating group.

3. The copolymer of claim 2, wherein $R^1$ is —CH$_3$, —NH$_2$, —NHC(O)OCH$_2$CH$_3$, or hydrogen.

4. The copolymer of claim 2, wherein the electron-donating group is $C_{1-6}$ alkyl, $C_{1-6}$ alkoxy, —OH, an amino group, $C_{1-6}$ hydroxyalkyl, $C_{1-6}$ alkylthio, or a carbamate.

5. The copolymer of claim 1, wherein the second constituent unit is represented by Formula II:

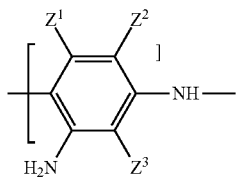
(II)

wherein $Z^1$, $Z^2$, and $Z^3$ are each independently hydrogen or an electron-donating group.

6. The copolymer of claim 5, wherein $Z^1$ is hydrogen, —$NH_2$, —$CH_3$, —OH, —$OCH_3$, or —$CH_2OH$.

7. The copolymer of claim 5, wherein $Z^2$ is hydrogen, —$OCH_3$, or —$SCH_3$.

8. The copolymer of claim 5, wherein $Z^3$ is hydrogen, —$OCH_3$, or —$CH_3$.

9. The copolymer of claim 1, wherein the second constituent unit is represented by Formula III, Formula IV, or Formula V:

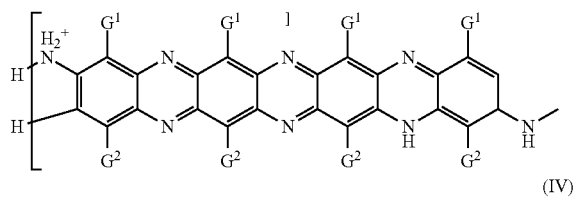
(III)

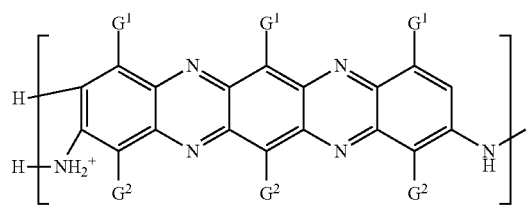
(IV)

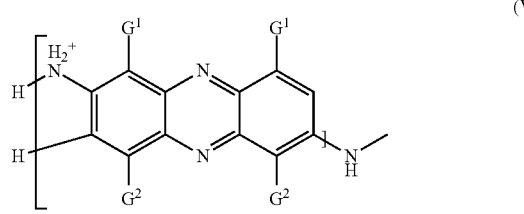
(V)

wherein $G^1$ and $G^2$ are each independently hydrogen or an electron-donating group.

10. The copolymer of claim 9, wherein $G^1$ and $G^2$ are each independently hydrogen or methoxy.

11. The copolymer of claim 1, wherein the copolymer has a molar ratio of the first constituent unit to the second constituent unit of about 5:95.

12. A polymeric membrane for ion sensitive measurement comprising an ethylene-vinyl acetate copolymer (EVA) and one or more ionophores that are selective toward lead ions, wherein the one or more ionophores include particles of a copolymer having at least one optionally substituted 2-hydroxy-5-sulfonic aniline as a first constituent unit and at least one optionally substituted phenylenediamine as a second constituent unit, wherein the first constituent unit is present in the copolymer in an amount of about 5% to about 10% by mole and the second constituent unit is present in the copolymer in an amount of about 90% to about 95% by mole, and wherein the particles of the copolymer have an average diameter of about 2000 nm.

13. The polymeric membrane of claim 12, wherein the first constituent unit is represented by Formula I:

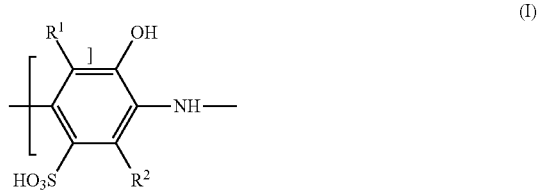
(I)

wherein $R^1$ is hydrogen or an electron-donating group, and $R^2$ is hydrogen or an electron-donating group.

14. The polymeric membrane of claim 13, wherein $R^1$ is —$CH_3$, —$NH_2$, —$NHC(O)OCH_2CH_3$, or hydrogen.

15. The polymeric membrane of claim 13, wherein the electron-donating group is $C_{1-6}$ alkyl, $C_{1-6}$ alkoxy, —OH, an amino group, $C_{1-6}$ hydroxyalkyl, $C_{1-6}$ alkylthio, or a carbamate.

16. The polymeric membrane of any one of claim 12, wherein the second constituent unit is represented by Formula II

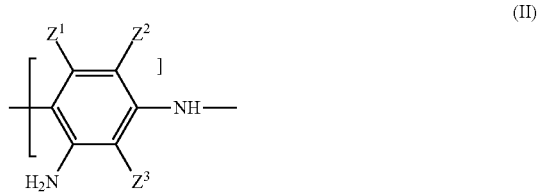
(II)

wherein $Z^1$, $Z^2$, and $Z^3$ are each independently hydrogen or an electron-donating group.

17. The polymeric membrane of claim 16, wherein:
$Z^1$ is hydrogen, —$NH_2$, —$CH_3$, —OH, —$OCH_3$, or —$CH_2OH$; or
$Z^2$ is hydrogen, —$OCH_3$, or —$SCH_3$; or
$Z^3$ is hydrogen, —$OCH_3$, or —$CH_3$.

18. The polymeric membrane of claim 12, wherein the second constituent unit is represented by Formula III, Formula IV, or Formula V:

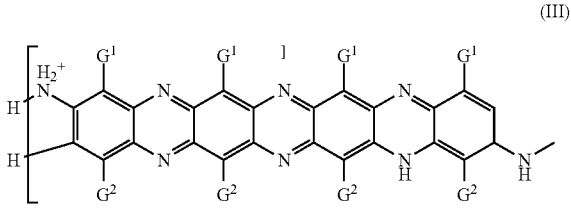
(III)

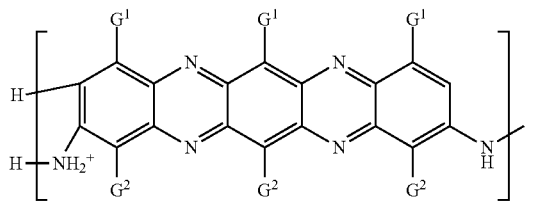
(IV)

-continued

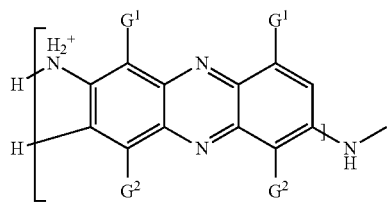

(V)

wherein G¹ and G² are each independently hydrogen or an electron-donating group.

19. The polymeric membrane of claim 18, wherein G¹ and G² are each independently hydrogen or methoxy.

20. The polymeric membrane of claim 12, wherein the polymeric membrane comprises the one or more ionophores in an amount of about 0.1% to about 10% by weight.

21. The polymeric membrane of claim 12, wherein the polymeric membrane comprises the one or more ionophores in an amount of about 4.5% by weight.

22. The polymeric membrane of claim 12, wherein the polymeric membrane comprises one or more ion exchangers.

23. The polymeric membrane of claim 22, wherein the polymeric membrane comprises the one or more ion exchangers in an amount of about 0% to about 8% by weight.

24. The polymeric membrane of claim 22, wherein the one or more ion exchangers are sodium tetraphenylborate (NaTPB), potassium tetraphenylborate (KTPB), potassium tetrakis(4-chlorophenyl)]borate (KTClPB), potassium tetrakis[3,5-bis(trifluoromethyl)phenyl]borate (KTFPB), sodium tetrakis[3,5-bis(trifluoromethyl)phenyl]borate (NaTFPB), or combinations thereof.

25. The polymeric membrane of claim 12, wherein the polymeric membrane has an average thickness of about 30 μm to about 400 μm.

26. The polymeric membrane of claim 12, wherein the polymeric membrane comprises one or more electrical conducting additives.

27. The polymeric membrane of claim 26, wherein the one or more electrical conducting additives comprise a conducting polymer, metal nanoparticles, a graphene nanosheet, a carbon nanotube, carbon black, polyaniline nanosticks, or any combination thereof.

28. The polymeric membrane of claim 27, wherein the conducting polymer comprises polyaniline, polypyrrole, polythiophene, polyacetylene, poly(3,4-ethylenedioxythiophene), poly(3-octylthiophene), or any combination thereof.

29. The polymeric membrane of claim 12, wherein the polymeric membrane is substantially plasticizer free.

30. A sensor for measuring lead ions, the sensor comprising: a lead ion-selective electrode, wherein the lead ion-selective electrode comprises a polymer matrix and particles of a copolymer, wherein the copolymer comprises at least one optionally substituted 2-hydroxy-5-sulfonic aniline as a first constituent unit and at least one optionally substituted phenylenediamine as a second constituent unit, wherein the first constituent unit is present in the copolymer in an amount of about 5% to about 10% by mole and the second constituent unit is present in the copolymer in an amount of about 90% to about 95% by mole, and wherein the particles of the copolymer have an average diameter of about 2000 nm.

31. The sensor of claim 30, wherein the sensor further comprises a reference electrode.

32. A method for detecting lead ions in a sample, the method comprising: providing a sample suspected of containing one or more lead ions;
contacting the sample with a sensor, wherein the sensor comprises a reference electrode and a lead ion-selective electrode, wherein the lead ion-selective electrode comprises a polymer matrix and one or more ionophores selective for lead ions, wherein the one or more ionophores comprise particles of a copolymer comprising at least one optionally substituted 2-hydroxy-5-sulfonic aniline as a first constituent unit and at least one optionally substituted phenylenediamine as a second constituent unit, wherein the first constituent unit is present in the copolymer in an amount of about 5% to about 10% by mole and the second constituent unit is present in the copolymer in an amount of about 90% to about 95% by mole, wherein the particles of the copolymer have an average diameter of about 2000 nm; and
measuring an electromotive force (EMF) between the reference electrode and the lead ion-selective electrode.

33. The method of claim 32, wherein the sensor is potentiometric and functions substantially logarithmically.

34. The method of claim 32, wherein the concentration of lead ions in the sample correlates with the EMF measured.

35. The method of claim 32, wherein the measured EMF is greater in the presence of the lead ions than in the absence of the lead ions.

36. The method of claim 32, wherein the concentration of the lead ions in the sample is about $10^{-3}$ M to about $10^{-7}$ M.

37. The method of claim 32, wherein the sample is contacted with the sensor for no more than about 10 minutes.

38. The method of claim 32, wherein the sample is contacted with the sensor for no more than about 60 seconds.

* * * * *